US007528127B2

(12) United States Patent
Feldman et al.

(10) Patent No.: US 7,528,127 B2
(45) Date of Patent: May 5, 2009

(54) SHORT-ACTING BENZODIAZEPINES

(75) Inventors: Paul L. Feldman, Research Triangle Park, NC (US); David Kendall Jung, Research Triangle Park, NC (US); Istvan Kaldor, Research Triangle Park, NC (US); Gregory J. Pacofsky, Research Triangle Park, NC (US); Jeffrey A. Stafford, Research Triangle Park, NC (US); Jeffrey H. Tidwell, Research Triangle Park, NC (US)

(73) Assignee: CeNes Limited, Cambridge (GB)

( * ) Notice: Subject to any disclaimer, the term of this patent is extended or adjusted under 35 U.S.C. 154(b) by 0 days.

(21) Appl. No.: 11/650,636

(22) Filed: Jan. 5, 2007

(65) Prior Publication Data

US 2007/0135420 A1    Jun. 14, 2007

Related U.S. Application Data

(62) Division of application No. 09/980,680, filed as application No. PCT/US00/13134 on May 12, 2000, now Pat. No. 7,160,880.

(30) Foreign Application Priority Data

May 14, 1999    (GB)    ................ 9911152.8

(51) Int. Cl.
*A61P 25/20* (2006.01)
*A61K 31/5517* (2006.01)
*C07D 487/02* (2006.01)

(52) U.S. Cl. ...................... 514/220; 540/561
(58) Field of Classification Search ................ 514/220; 540/561
See application file for complete search history.

(56) References Cited

U.S. PATENT DOCUMENTS

| | | | | |
|---|---|---|---|---|
| 4,755,508 | A | 7/1988 | Bock et al. | 514/221 |
| 5,324,726 | A | 6/1994 | Bock et al. | 514/221 |
| 5,665,718 | A | 9/1997 | Godel et al. | 514/220 |
| 5,698,691 | A | 12/1997 | Yukimasa et al. | 540/490 |
| 5,834,464 | A | 11/1998 | Bock et al. | 514/220 |
| 7,160,880 | B1 | 1/2007 | Feldman et al. | 514/221 |
| 2002/0055500 | A1 | 5/2002 | Wu et al. | 514/212.03 |

FOREIGN PATENT DOCUMENTS

| | | |
|---|---|---|
| CH | 608 234 | 12/1978 |
| DE | 40183 | 12/1959 |
| EP | 0100906 | 2/1984 |
| EP | 0 122 889 | 10/1984 |
| EP | 166356 | 1/1986 |
| EP | 167919 | 1/1986 |
| EP | 0 264 797 A | 4/1988 |
| EP | 284256 | 9/1988 |
| EP | 434360 | 6/1991 |
| EP | 4343364 | 6/1991 |
| EP | 0 508 798 A | 10/1992 |
| EP | 523845 | 1/1993 |
| EP | 176 927 | 9/1993 |
| EP | 727215 | 1/1996 |
| EP | 881 235 A | 12/1998 |
| FR | 2 034 577 A | 12/1970 |
| FR | 2 115 265 A | 7/1972 |
| FR | 2 183 716 A | 12/1973 |
| FR | 2 231 385 A | 12/1974 |
| FR | 2414043 A | 8/1979 |
| GB | 2259013 | 3/1993 |
| NL | 7012813 | 8/1970 |
| WO | WO 91 05549 | 5/1991 |
| WO | WO 96 23790 | 8/1995 |
| WO | WO 96 20941 | 7/1996 |
| WO | WO 98 00405 | 1/1998 |
| WO | WO 98/38177 | 9/1998 |

OTHER PUBLICATIONS

Ichihara, Masato et al., "Preparation of diazepine derivatives as specific inhibitors of human renin", *Database Chemabs Online, Chemical Abstracts Service*, (1995).

Goumri-Magnet S. Et al., "Free and Supported Phosphorus Ylides as Strong Neutral Bronsted Bases", *Journal of Organic Chemistry*, vol. 64, No. 10, (1999), pp. 3741-3744.

Avdagic, Amir et al., "Lipase-catalyzed acetylation of 3-substituted 2,3-dihydro-1H-1,4-bezodiazepin-2-ones. Effect of temperature and conformation on enantioselectivity and configuration", *Helv. Chim. Acta*, vol. 81, No. 8, pp. 1567-1582, (1998).

Heaney Frances et al., "Steric control of reactivity: formation of oximes, benzodiazepinone N-oxides and isoxazoloquinolinones", *Journal Chem. Soc.*, Perkin Trans. vol. 2, (3), (1998), pp. 547-559.

Bock, Mark G. et al., "Curtius rearrangement in the 5-phenyl-1, 4-benzodiazepine series. Unprecedented participation by an imine nitrogen", *Journal Heterocycl. Chem.*, vol. 27, No. 3, (1990), pp. 631-636.

(Continued)

*Primary Examiner*—Brenda L Coleman
(74) *Attorney, Agent, or Firm*—Peter F. Corless; Edwards Angell Palmer & Dodge LLP

(57) ABSTRACT

It has now been found that compounds of the present invention as described in Benzodiazepine derivatives of Formula (I) containing a carboxylic ester moiety and thereby capable of being inactivated by nonspecific tissue esterases in an organ-independent elimination mechanism and thereby providing a more predictable and reproducible pharmacodynamic profile. The compounds of the present invention are suitable for therapeutic purposes, including sedative-hypnotic, anxiolytic, muscle relaxant and anticonvulsant purposes and are useful to be administered intravenously in the following clinical settings: preoperative sedation, anxiolysis, and amnestic use for perioperative events; conscious sedation during short diagnostic, operative or endoscopic procedures; as a component for the induction and maintenance of general anesthesia, prior and/or concomitant to the administration of other anesthetic agents; ICU sedation.

10 Claims, No Drawings

OTHER PUBLICATIONS

Manghisi, E. et al., Synthesis and central nervous effects of some 3-substituted 1,4-benzodiazepin-2-ones, *Boll Chim. Farm.*, vol. 113, No. 12, (1974), pp. 642-644.

Corbella, Attilio et al., "Stereochemistry of the enymic 3-hydroxylation of 1,3-dihydro-22H-1,4-benzodiazepin-2-ones", *J. Chem. Soc., Chem.* Commun., No. 19, (1973), pp. 721-722.

Walser, Armin et al., "Quinazolines and 1,4-benzodiazepines. LIX. Preparation of pyrrolo '2, 1-c-1,4-benzodiazepines", *J. Org. Chem.*, vol. 38, No. 20, (1973), pp. 3502-3507.

Shimamoto, Kiro et al., "Pharmaceutical screening of new benzodiazepines in mice", *Takeda Kenkyusho Ho*, vol. 29, No. 1 (1970) pp. 134-144.

Gilman, A.G., et al. "Goodman and Filman's The Pharmacological Basis of Therapeutics." Eighth Edition, Pergamon Press: New York, 1990; pp. 303-304, 346-358.

Hering W., et al. "CNS Effects of the New Benzodiazepines RO 48-6791 and RO 48-8684 Compared to Midazolam in Young and Elderly Volunteers." Anesthesiology 1996, 189,85 (Suppl.).

Dingemanse, J. et al. "Pharmacokinetic-Pharmacodynamic Modeling of the EEF Effects of RO 48-6791, a New Short-Acting Benzodiazepine, in Young and Elderly Subjects." Br. J. Anaesth 1997, 79, pp. 567-574.

Khan, W.A., et al. "Synthesis of 3-Substituted 1,4-Benzodiazepine2-Ones." Org. Prep. Proc. Int., 1978, 10, pp. 105-111.

Hester, J.B., et al. "8-Chloro-1-methyl-6-phenyl-4H-s-triazolo [4,3-a][1,4]benzodiazepines with Substituents at C-4", J. Med Chem., 1980, 23, 643-647.

Bauer, T.M., et al. "Prolonged Sedation Due to Accumulation of Conjugated Metabolites of Midazolam." Lancet 1995, 346, pp. 145-147.

Shafer, A., et al. "Complications of Sedation with Midazolam in the Intensive Care Unit and a Comparison with Other Sedative Regiments." Crit Care Med., 1998, 26, 947-956.

SHORT-ACTING BENZODIAZEPINES

CROSS REFERENCE TO RELATED APPLICATIONS

This application is a divisional of U.S. application Ser. No. 09/980,680 filed Oct. 31, 2001, which is a national entry Rule 371 Application of PCT Application No. US00/13134 filed May 12, 2000, which claims priority to GB application Serial no. 9911152.8 filed May 14, 1999.

FIELD OF THE INVENTION

The present invention relates to benzodiazepine derivatives, to pharmaceutical compositions containing them and to their use in medicine. More particularly, the present invention relates to benzodiazepine derivatives suitable for therapeutic purposes, including sedative-hypnotic, anxiolytic, muscle relaxant and anticonvulsant purposes.

BACKGROUND OF THE INVENTION

The broad neuropharmacology elicited from the benzodiazepine class of compounds is generally attributed to their binding to a site on a specific receptor/chloride ion channel complex known as the $GABA_A$ receptor. Benzodiazepine-receptor binding potentiates the binding of the inhibitory neurotrarsmitter γ-aminobutyric acid (GABA) to the complex, thereby leading to inhibition of normal neuronal function. In addition to the therapeutic purposes listed above, benzodiazepines have been used widely for anesthesia, particularly as a premedication or as a component in the induction and/or maintenance of anesthesia. See generally, *Goodman and Gilman's The Pharmacological Basis of Therapeutics, Eighth Edition*; Gilman, A. G.; Rall, T. W.; Nies, A. S.; Taylor, P., Eds.; Pergamon Press: New York, 1990; pp. 303-304, 346-358.

Shorter-acting benzodiazepines that may provide faster recovery profiles have been the subject of recent clinical investigations (W. Hering et al., *Anesthesiology* 1996, 189, 85 (Suppl.); J. Dingemanse et al., *Br. J. Anaesth* 1997, 79, 567-574.) Recent patent filings also describe benzodiazepines of interest. (WO 96/23790; WO 96/20941; U.S. Pat. No. 5,665, 718). Other publications that describe benzodiazepinones include E. Manghisi and A. Salimbemi, *Boll. Chim. Farm.* 1974, 113, 642-644), W. A. Khan and P. Singl, *Org. Prep. Proc. Int.* 1978, 10, 105-111 and J. B. Hester, Jr, et al. *J. Med. Chem.* 1980, 23, 643-647. Benzodiazepines in present practice, such as diazepam, lorazepam, and midazolam all undergo metabolism by hepatic-dependent processes. Active metabolites, which are often much more slowly metabolized than the parent drug, can be generated by these hepatic mechanisms in effect prolonging the duration of action of many benzodiazepines (T. M. Bauer et al., *Lancet* 1995, 346, 145-7). Inadvertent oversedation has been associated with the use of benzodiazepines (A. Shafer, *Crit Care Med* 1998, 26, 947-956), particularly in the ICU, where benzodiazepines, such as midazolam, enjoy frequent use. However, the benzodiazepine compounds of this invention differ from benzodiazepines in present-day clinical practice.

SUMMARY OF THE INVENTION

It has now been found that compounds of the present invention as described in Formula (I) possess certain advantages because of their structural design. The benzodiazepines described by this invention all contain a carboxylic ester moiety and are inactivated by nonspecific tissue esterases. An organ-independent elimination mechanism is predicted to be characteristic of the benzodiazepines of this invention, providing a more predictable and reproducible pharmacodynamic profile.

The compounds of the present invention are suitable for therapeutic purposes, including sedative-hypnotic, anxiolytic, muscle relaxant and anticonvulsant purposes. The compounds of the present invention are short-acting CNS depressants that are useful to be administered intravenously in the following clinical settings: preoperative sedation, anxiolysis, and amnestic use for perioperative events; conscious sedation during short diagnostic, operative or endoscopic procedures; as a component for the induction and maintenance of general anesthesia, prior and/or concomitant to the administration of other anesthetic agents; ICU sedation.

DETAILED DESCRIPTION OF THE INVENTION

Thus it is provided according to a first aspect of the present invention compounds of Formula (I):

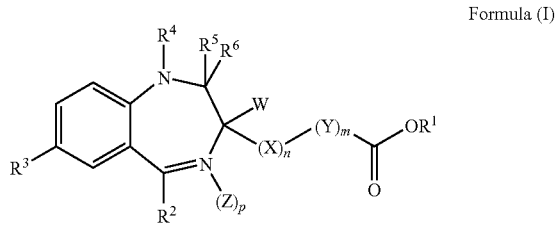

Formula (I)

wherein
W is H, $C_1$-$C_4$ branched alkyl, or a straight chained alkyl;
X is $CH_2$, NH, or $NCH_3$; n is 1 or 2;
Y is O or $CH_2$; m is 0 or 1, provided that if X is $CH_2$, n is 1 and m is 0, then $R^1$ is not $CH_2CH_3$;
Z is O; p is 0 or 1;
$R^1$ is H, a $C_1$-$C_7$ straight chain alkyl, a $C_3$-$C_7$ branched chain alkyl, a $C_1$-$C_4$haloalkyl, a $C_3$-$C_7$ cycloalkyl, an aryl, a heteroaryl, an aralkyl, or a heteroaralkyl;
$R^2$ is phenyl, 2-halophenyl, or 2-pyridyl,
$R^3$ is H, Cl, Br, F, I, $CF_3$, or $NO_2$;
(1) $R^4$ is H, $C_1$-$C_4$ alkyl, or dialkylaminoalkyl and $R^5$ and $R^6$ together represent a single oxygen or S atom which is linked to the diazepine ring by a double bond and p is zero or 1 (as depicted in formula Ia); or (2) $R^4$ and $R^5$ together form a double bond in the diazepine ring and $R^6$ represents the group $NHR^7$ wherein $R^7$ is H, $C_{1-4}$ alkyl, $C_{1-4}$ hydroxyalkyl, benzyl or benzyl mono or disubstituted independently with halogen substituents, $C_{1-4}$alkylpyridyl or $C_{1-4}$ alkylimidazolyl and p is zero (as depicted in formula Ib); or (3) $R^4$, and $R^6$ form the group —$CR^8$=U—V= wherein $R^8$ is hydrogen, $C_{1-4}$ alkyl or $C_{1-3}$ hydroxyalkyl, U is N or $CR^9$ wherein $R^9$ is H, $C_{1-4}$alkyl, $C_{1-3}$ hydroxyalkyl or $C_{1-4}$alkoxy-$C_{1-4}$alkyl, V is N or CH and p is zero (as depicted in formula Ic);

or pharmaceutically acceptable salts and or solvates thereof.
The term "aryl," alone or in combination, is defined herein as a monocyclic or polycyclic group, preferably a monocyclic or bicyclic group, e.g., phenyl or naphthyl, which can be unsubstituted or substituted, for example, with one or more and, in particular, one to three substituents selected from halogen, $C_1$-$C_4$ branched or straight chained alkyl, $C_1$-$C_4$ alkoxy, $C_1$-$C_4$ haloalkyl, hydroxy, nitro, amino, and the like.

The term "heteroaryl" is defined herein as a 5-membered or 6-membered heterocyclic aromatic group which can optionally carry a fused benzene ring and wherein said 5-membered or 6-membered heterocyclic aromatic group can be unsubstituted or substituted, for example, with one or more and, in particular, one to three substituents selected from halogen, $C_1$-$C_4$ branched or straight chained alkyl, $C_1$-$C_4$ alkoxy, $C_1$-$C_4$ haloalkyl, hydroxy, nitro, amino, and the like. The term "alkoxy," alone or in combination, is defined herein to include an alkyl group, as defined earlier, which is attached through an oxygen atom to the parent molecular subunit. Exemplary alkoxy groups include but are not necessarily limited to methoxy, ethoxy and isopropoxy. The term "aralkyl" is defined herein as an alkyl group, as defined earlier, in which one of the hydrogen atoms is replaced by an aryl group. The term "heteroaralkyl" is defined herein as an alkyl group, as defined earlier, in which one of the hydrogen atoms is replaced by a heteroaryl group.

Exemplary branched or straight chained $C_1$-$C_4$ alkyl groups include but are not necessarily limited to methyl, ethyl, propyl, isopropyl, isobutyl and n-butyl. Exemplary $C_1$-$C_7$ straight chain alkyl groups include, but are not necessarily limited to, methyl, ethyl, propyl, n-butyl, n-hexyl and n-heptyl. Exemplary $C_3$-$C_7$ branched chain alkyl groups include, but are not necessarily limited to, isopropyl, isobutyl, sec-butyl, tert-butyl, isopentyl, neopentyl, tert-pentyl and isohexyl. Exemplary $C_3$-$C_7$ cycloalkyl groups include, but are not necessarily limited to, cyclopropyl, cyclobutyl, cyclopentyl, cyclohexyl and cycloheptyl. Exemplary $C_1$-$C_4$ haloalkyl groups include, but are not necessarily limited, to methyl, ethyl, propyl, isopropyl, isobutyl and n-butyl substituted independently with one or more halogens, e.g., fluoro, chloro, bromo and iodo.

The compounds of formula (I) wherein $R^5$ and $R^6$ together represent an oxygen or sulphur atom linked to the diazepine ring via a double bond represent a first embodiment of a first aspect of the present invention and are conveniently represented by the formula (1a):

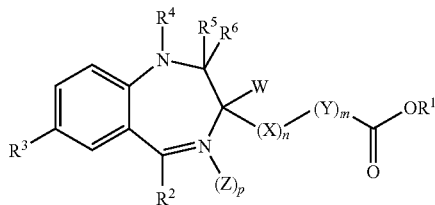

(1a)

wherein $R^1$, $R^2$, $R^3$, W, X, Y, Z, p, n and m have the meanings defined in formula (I).

In one embodiment of the compounds of formula (1a) there are provided compounds wherein
W is H;
X is $CH_2$ or NH; n is 1;
Y is $CH_2$; m is 0 or 1, provided that if X is $CH_2$, n is 1 and m is 0, then $R^1$ is not $CH_2CH_3$;
Z is O; p is 0 or 1;
$R^1$ is H, $CH_3$, $CH_2CH_3$, $(CH_2)_2CH_3$, $(CH_2)_3CH_3$, $CH_2(CH_3)_2$, $CH_2CH(CH_3)_2$, $C(CH_3)_3$, benzyl, 4-pyridylmethyl or 3-pyridylmethyl;
$R^2$ is phenyl, 2-fluorophenyl, 2-chlorophenyl or 2-pyridyl;
$R^3$ is Cl, Br or $NO_2$;
$R^4$ is H, $CH_3$ or $CH_2CH_2N(CH_2CH_3)_2$;
$R^5$ and $R^6$ together are O or S; or pharmaceutically acceptable salts and solvates thereof.

A further embodiment of the compounds of formula (Ia) is that wherein:
W is H;
X is $CH_2$ or NH; n is 1;
Y is $CH_2$; m is 1;
p is 0;
$R^1$ is H, $CH_3$, $CH_2CH_3$. $(CH_2)_2CH_3$, $(CH_2)_3CH_3$, $CH_2(CH_3)_2$, $CH_2CH(CH_3)_2$, $C(CH_3)_3$, benzyl, 4-pyridylmethyl or 3-pyridylmethyl; provided that if $R^1$ is 3-pyridylmethyl or 4-pyridylmethyl, then X is $CH_2$, n is 1, Y is $CH_2$, m is 0 or 1, $R^2$ is 2-fluorophenyl, $R^3$ is Cl, $R^4$ is H and $R^5$ and $R^6$ together is oxygen;
$R^2$ is phenyl, 2-fluorophenyl, 2-chlorophenyl or 2-pyridyl,
$R^3$ is Cl, Br or $NO_2$;
$R^4$ is H, $CH_3$ or $CH_2CH_2N(CH_2CH_3)_2$; provided that when $R^4$ $CH_2CH_2N(CH_2CH_3)_2$, then X is $CH_2$, n is 1, Y is $CH_2$, m is 1, $R^1$ is $CH_3$ or benzyl, $R^2$ is 2-fluorophenyl, $R^3$ is Cl and $R^5$ and $R^6$ together represent O;
$R^5$ and $R^6$ together are O or S; or pharmaceutically acceptable salts and solvates thereof.

In yet a further embodiment of the present invention are the compounds of formula (1a) wherein
W is H;
X is $CH_2$ or NH; n is 1;
Y is $CH_2$; m is 0 or 1, provided that if X is $CH_2$ and m is 0, then $R^1$ is not $CH_2CH_3$;
p is 0;
$R^1$ is $CH_3$, $CH_2CH_3$, $(CH_2)_2CH_3$, $(CH_2)_3CH_3$, $CH_2(CH_3)_2$, $CH_2CH(CH_3)_2$, $C(CH_3)_3$, benzyl or 4-pyridylmethyl;
$R^2$ is 2-fluorophenyl, 2-chlorophenyl or 2-pyridyl,
$R^3$ is Cl, Br or $NO_2$;
$R^4$ is H, $CH_3$ or $CH_2CH_2N(CH_2CH_3)_2$;
$R^5$ and $R^6$ together are O or S; or pharmaceutically acceptable salts and solvates thereof.

Yet another embodiment of the present invention are compounds of formula (Ia) wherein
W is H;
X is $CH_2$ or NH; n is 1;
Y is $CH_2$; m is 0 or 1, provided that if X is $CH_2$ and m is 0, then $R^1$ is not $CH_2CH_3$;
p is 0;
$R^1$ is $CH_3$, $CH_2CH_3$, $(CH_2)_2CH_3$, $(CH_2)_3CH_3$, $CH_2(CH_3)_2$, $CH_2CH(CH_3)_2$, $C(CH_3)_3$, benzyl or 4-pyridylmethyl; provided that when $R^1$ is 4-pyridylmethyl, then X is $CH_2$, Y is $CH_2$, m is 1, $R^2$ is 2-fluorophenyl, $R^3$ is Cl, $R^4$ is H and $R^5$ and $R^6$ together represent oxygen;
$R^2$ is 2-fluorophenyl, 2-chlorophenyl or 2-pyridyl,
$R^3$ is Cl, Br or $NO_2$;
$R^4$ is H, $CH_3$ or $CH_2CH_2N(CH_2CH_3)_2$; provided that when $R^4$ is $CH_2CH_2N(CH_2CH_3)_2$, then X is $CH_2$, Y is $CH_2$, m is 1, $R^1$ is $CH_3$ or benzyl, $R^2$ is 2-fluorophenyl, $R^3$ is Cl and $R^5$ and $R^6$ together represent O;
$R^5$ and $R^6$ together represent O or S; or pharmaceutically acceptable salts and solvates thereof.

Yet another embodiment of the first aspect of the invention are compounds of formula (Ia) or pharmaceutically acceptable salts and solvates thereof wherein in each compound W is H and wherein X, n, Y, m, Z, p and $R^{1-6}$ for each compound are as follows:

| X | n | Y | m | Z | p | R¹ | R² | R³ | R⁴ | R⁵ and R⁶ |
|---|---|---|---|---|---|---|---|---|---|---|
| CH₂ | 1 | CH₂ | 1 | — | 0 | CH₃ | 2-fluorophonyl | Cl | H | O |
| CH₂ | 1 | — | 0 | — | 0 | CH₃ | 2-fluorophenyl | Cl | H | O |
| CH₂ | 1 | CH₂ | 1 | — | 0 | CH₃ | 2-fluorophenyl | Br | H | O |
| CH₂ | 1 | CH₂ | 1 | — | 0 | benzyl | 2-fluorophenyl | Cl | H | O |
| CH₂ | 1 | — | 0 | — | 0 | benzyl | 2-fluorophenyl | Cl | H | O |
| CH₂ | 1 | CH₂ | 1 | — | 0 | CH₃ | 2-chlorophenyl | Cl | H | O |
| CH₂ | 1 | CH₂ | 2 | — | 0 | CH₃ | 2-fluorophenyl | Cl | H | O |
| CH₂ | 1 | CH₂ | 1 | — | 0 | benzyl | 2-pyridyl | Cl | H | O |
| CH₂ | 1 | CH₂ | 1 | — | 0 | CH₃ | 2-pyridyl | Br | H | O |
| CH₂ | 1 | CH₂ | 1 | — | 0 | CH₃ | 2-pyridyl | Cl | H | O |
| CH₂ | 1 | CH₂ | 2 | — | 0 | C(CH₃)₃ | 2-fluorophenyl | Cl | H | O |
| CH₂ | 1 | CH₂ | 1 | — | 0 | CH₃ | 2-fluorophenyl | NO₂ | H | O |
| CH₂ | 1 | CH₂ | 1 | — | 0 | (CH₂)₂CH₃ | 2-pyridyl | Cl | H | O |
| CH₂ | 1 | CH₂ | 1 | — | 0 | —CH₂CH₃ | 2-pyridyl | Cl | H | O |
| CH₂ | 1 | CH₂ | 1 | — | 0 | 4-pyridyl-methyl | 2-fluorophenyl | Cl | H | O |
| CH₂ | 1 | CH₂ | 1 | — | 0 | (CH₂)₃CH₃ | 2-fluorophenyl | Cl | H | O |
| CH₂ | 1 | CH₂ | 1 | — | 0 | (CH₂)₃CH₃ | 2-pyridyl | Cl | H | O |
| CH₂ | 1 | CH₂ | 1 | — | 0 | CH₂CH(CH₃)₂ | 2-pyridyl | Cl | H | O |
| CH₂ | 1 | — | 0 | — | 0 | CH₂CH₃ | 2-fluorophenyl | Cl | H | O |
| CH₂ | 1 | CH₂ | 1 | — | 0 | CH(CH₃)₂ | 2-fluorophenyl | Cl | H | O |
| CH₂ | 1 | CH₂ | 1 | — | 0 | CH₃ | 2-fluorophenyl | Cl | CH₂CH₂N—(CH₂CH₃)₂ | O |
| CH₂ | 1 | CH2 | 1 | — | 0 | CH₃ | 2-fluorophenyl | Cl | CH₃ | O |
| CH₂ | 1 | — | 0 | — | 0 | benzyl | 2-fluorophenyl | Cl | CH₃ | O |
| CH₂ | 1 | CH₂ | 1 | — | 0 | benzyl | 2-fluorophenyl | Cl | CH₂CH₂N—(CH₂CH₃)₂ | O |
| NH | 1 | CH₂ | 1 | — | 0 | CH₃ | 2-chlorophenyl | Cl | H | O |
| NH | 1 | CH₂ | 2 | — | 0 | CH₃ | 2-chlorophenyl | Cl | H | O |
| CH₂ | 1 | CH₂ | 1 | — | 0 | CH₃ | 2-fluorophenyl | Cl | H | S |
| CH₂ | 1 | CH₂ | 1 | — | 0 | CH₃ | 2-chlorophenyl | Cl | H | S |
| CH₂ | 1 | CH₂ | 1 | — | 0 | CH₃ | 2-pyridyl | Cl | H | S |
| CH₂ | 1 | CH₂ | 1 | O | 1 | CH₃ | 2-fluorophenyl | Cl | H | O |
| CH₂ | 1 | CH₂ | 1 | — | 0 | benzyl | phenyl | NO₂ | H | O |
| CH₂ | 1 | CH₂ | 1 | — | 0 | CH₃ | 2-fluorophenyl | H | H | O |
| CH₂ | 1 | CH₂ | 1 | — | 0 | CH₃ | 2-pyridyl | NO₂ | H | O |
| CH₂ | 1 | CH₂ | 1 | — | 0 | benzyl | 2-pyridyl | NO₂ | H | O |
| CH₂ | 1 | CH₂ | 1 | — | 0 | benzyl | 2-fluorophenyl | H | H | O |
| CH₂ | 1 | CH₂ | 1 | — | 0 | CH₃ | phenyl | NO₂ | H | O |
| NH | 1 | CH₂ | 2 | — | 0 | (CH₂)₃CH₃ | 2-fluorophenyl | Cl | H | O |
| CH₂ | 1 | — | 0 | — | 0 | 3-pyridyl-methyl | 2-fluorophenyl | Cl | H | O |
| CH₂ | 1 | — | 0 | — | 0 | 4-pyridyl-methyl | 2-fluorophenyl | Cl | H | O |

Yet another embodiment of the first aspect of the invention are compounds of formula (Ia) or pharmaceutically acceptable salts and solvates thereof wherein in each compound W is H and wherein X, n, Y, m, Z, p and $R^{1-6}$ for each compound are as follows:

| X | n | Y | m | Z | p | R¹ | R² | R³ | R⁴ | R⁵ and R⁶ |
|---|---|---|---|---|---|---|---|---|---|---|
| CH₂ | 1 | CH₂ | 1 | — | 0 | CH₃ | 2-fluorophenyl | Cl | H | O |
| CH₂ | 1 | — | 0 | — | 0 | CH₃ | 2-fluorophenyl | Cl | H | O |
| CH₂ | 1 | CH₂ | 1 | — | 0 | CH₃ | 2-fluorophenyl | Br | H | O |
| CH₂ | 1 | CH₂ | 1 | — | 0 | benzyl | 2-fluorophenyl | Cl | H | O |
| CH₂ | 1 | — | 0 | — | 0 | benzyl | 2-fluorophenyl | Cl | H | O |
| CH₂ | 1 | CH₂ | 1 | — | 0 | CH₃ | 2-chlorophenyl | Cl | H | O |
| CH₂ | 1 | CH₂ | 2 | — | 0 | CH₃ | 2-fluorophenyl | Cl | H | O |
| CH₂ | 1 | CH₂ | 1 | — | 0 | benzyl | 2-pyridyl | Cl | H | O |
| CH₂ | 1 | CH₂ | 1 | — | 0 | CH₃ | 2-pyridyl | Br | H | O |
| CH₂ | 1 | CH₂ | 1 | — | 0 | CH₃ | 2-pyridyl | Cl | H | O |
| CH₂ | 1 | CH₂ | 2 | — | 0 | C(CH₃)₃ | 2-fluorophenyl | Cl | H | O |
| CH₂ | 1 | CH₂ | 1 | — | 0 | CH₃ | 2-fluorophenyl | NO₂ | H | O |
| CH₂ | 1 | CH₂ | 1 | — | 0 | (CH₂)₂CH₃ | 2-pyridyl | Cl | H | O |
| CH₂ | 1 | CH₂ | 1 | — | 0 | CH₂CH₃ | 2-pyridyl | Cl | H | O |
| CH₂ | 1 | CH₂ | 1 | — | 0 | 4-pyridylmethyl | 2-fluorophenyl | Cl | H | O |
| CH₂ | 1 | CH₂ | 1 | — | 0 | (CH₂)₃CH₃ | 2-fluorophenyl | Cl | H | O |
| CH₂ | 1 | CH₂ | 1 | — | 0 | (CH₂)₃CH₃ | 2-pyridyl | Cl | H | O |
| CH₂ | 1 | CH₂ | 1 | — | 0 | CH₂CH(CH₃)₂ | 2-pyridyl | Cl | H | O |
| CH₂ | 1 | — | 0 | — | 0 | CH₂CH₃ | 2-fluorophenyl | Cl | H | O |
| CH₂ | 1 | CH₂ | 1 | — | 0 | CH(CH₃)₂ | 2-fluorophenyl | Cl | H | O |
| CH₂ | 1 | CH₂ | 1 | — | 0 | CH₃ | 2-fluorophenyl | Cl | CH₂CH₂N(CH₂CH₃)₂ | O |
| CH₂ | 1 | CH₂ | 1 | — | 0 | CH₃ | 2-fluorophenyl | Cl | CH₃ | O |

-continued

| X | n | Y | m | Z | p | R¹ | R² | R³ | R⁴ | R⁵ and R⁶ |
|---|---|---|---|---|---|---|---|---|---|---|
| CH₂ | 1 | — | 0 | — | 0 | benzyl | 2-fluorophenyl | Cl | CH₃ | O |
| CH₂ | 1 | CH₂ | 1 | — | 0 | benzyl | 2-fluorophenyl | Cl | CH₂CH₂N(CH₂CH₃)₂ | O |
| NH | 1 | CH₂ | 1 | — | 0 | CH₃ | 2-chlorophenyl | Cl | H | O |
| NH | 1 | CH₂ | 2 | — | 0 | CH₃ | 2-chlorophenyl | Cl | H | O |
| CH₂ | 1 | CH₂ | 1 | — | 0 | CH₃ | 2-fluorophenyl | Cl | H | S |
| CH₂ | 1 | CH₂ | 1 | — | 0 | CH₃ | 2-chlorophenyl | Cl | H | S |
| CH₂ | 1 | CH₂ | 1 | — | 0 | CH₃ | 2-pyridyl | Cl | H | S |
| CH₂ | 1 | CH₂ | 1 | O | 1 | CH₃ | 2-fluorophenyl | Cl | H | O |

Yet another embodiment of the first aspect of the invention are compounds of formula (Ia) or pharmaceutically acceptable salts and solvates thereof wherein in each compound W is H, and p is 0, and wherein X, n, Y, m, $R^{1-6}$ for each compound are as follows:

| X | n | Y | m | R¹ | R² | R³ | R⁴ | R⁵ and R⁶ |
|---|---|---|---|---|---|---|---|---|
| CH₂ | 1 | CH₂ | 1 | CH₃ | 2-fluorophenyl | Cl | H | O |
| CH₂ | 1 | CH₂ | 1 | CH₃ | 2-fluorophenyl | Br | H | O |
| CH₂ | 1 | CH₂ | 1 | CH₃ | 2-pyridyl | Cl | H | O |
| CH₂ | 1 | CH₂ | 1 | CH₃ | 2-fluorophenyl | Cl | CH₃ | O |

Yet another embodiment of the first aspect of the invention is a compound of formula (Ia) or a pharmaceutically acceptable salt and solvate thereof wherein W is H, X is $CH_2$, n is 1, Y is $CH_2$, m is 1, p is 0, $R^1$ is $CH_3$, $R^2$ is 2-fluorophenyl, $R^3$ is Cl, $R^4$ is H and $R^5$ and $R^6$ together represent oxygen.

The compounds of formula (I) wherein $R^4$ and $R^5$ together form a double bond in the diazepine ring and wherein $R^6$ is the group $NHR^7$ represent a further embodiment of the first aspect of the invention and are conveniently represented by formula (1b).

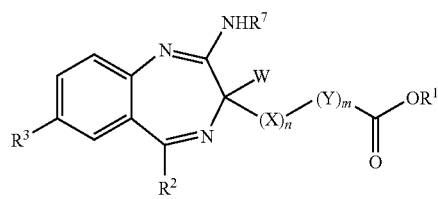

Formula (Ib)

wherein $R^1$, $R^2$, $R^4$, $R^7$, W, X, Y, n and m have the meanings defined in formula (I).

In a further embodiment of the first aspect of the invention are compounds of formula (Ib) or pharmaceutically acceptable salts and solvates thereof wherein W is H, X is $CH_2$, n is 1, Y is $CH_2$, m is 1, $R^1$ is $CH_3$, $R^2$ is 2-fluorophenyl, 2-chlorophenyl or 2-pyridyl, $R^3$ is Cl or Br and $R^7$ is $CH_3$, $CH_2CH_3$, benzyl, 4-pyridylmethyl-, 4-pyridylethyl, $CH(CH_3)_2$, 4-imidazolylethyl or $CH_2CH_2OH$.

In yet another embodiment of the first aspect of the invention are compounds of formula (Ib) or pharmaceutically acceptable salts and solvates thereof wherein in each compound W is H, X is $CH_2$, n is 1, Y is $CH_2$, m is 1, $R^1$ is $CH_3$, and wherein $R^2$, $R^3$ and $R^7$ for each compound are as follows:

| R² | R³ | R⁷ |
|---|---|---|
| 2-fluorophenyl | Cl | CH₃ |
| 2-pyridyl | Cl | CH₃ |
| 2-fluorophenyl | Cl | CH₂CH₃ |
| 2-fluorophenyl | Cl | benzyl |
| 2-fluorophenyl | Cl | 4-pyridylmethyl |
| 2-fluorophenyl | Cl | 4-pyridylethyl |
| 2-fluorophenyl | Cl | CH₂CH(CH₃)₂ |
| 2-fluorophenyl | Cl | 2-(4-imidazolyl)ethyl |
| 2-fluorophenyl | Cl | CH₂CH₂OH |
| 2-fluorophenyl | Br | CH₃ |
| 2-chlorophenyl | Cl | CH₃ |

Yet another embodiment of the first aspect of the invention are compounds of formula (Ib) or pharmaceutically acceptable salts and solvates thereof wherein in each compound W is H, X is $CH_2$, n is 1, Y is $CH_2$, m is 1, $R^1$ is $CH_3$, $R^2$ is 2-fluorophenyl, $R^3$ is chlorine or bromine and $R^7$ is methyl.

Yet another embodiment of the first aspect of the invention is a compound of formula (Ib) or a pharmaceutically acceptable salt and solvate thereof wherein W is H, X is $CH_2$, n is 1, Y is $CH_2$, m is 1, $R^1$ is $CH_3$, $R^2$ is 2-fluorophenyl, $R^3$ is Cl and $R^4$ is $CH_3$.

The compounds of formula (I) where the groups $R^4$ and $R^5$ and $R^6$ together form the group $-CR^8=U-V=$ represent a further embodiment of the first aspect of the invention and may be conveniently represented by the compound of formula (1c):

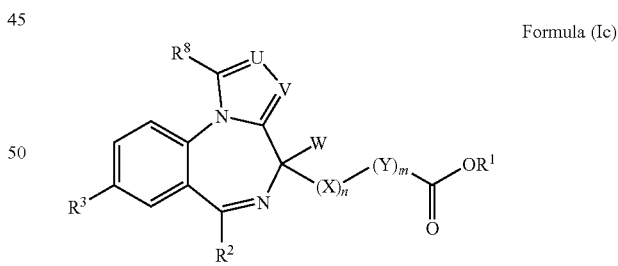

Formula (Ic)

wherein $R^1$, $R^2$, $R^8$, U, V, W, X, Y, n and m have the meanings given in formula (I).

In yet another embodiment of the first aspect of the invention are compounds of formula (Ic) or pharmaceutically acceptable salts and solvates thereof wherein
W is H,
X is $CH_2$, n is 1;
Y is $CH_2$, m is 1;
$R^1$ is $CH_3$ or $CH_2CH(CH_3)_2$;
$R^2$ is 2-fluorophenyl, 2-chlorophenyl or 2-pyridyl;
$R^3$ is Cl or Br;

$R^8$ is H, $CH_3$ or $CH_2OH$;
$R^9$ is H, $CH_3$, $CH_2OH$ or $CH_2O$-t-butyl;
U is $CR^9$ or N; and
V is N or CH.

Yet another embodiment of the first aspect of the invention are compounds of formula (Ic) or pharmaceutically acceptable salts and solvates thereof wherein
W is H,
X is $CH_2$, n is 1;
Y is $CH_2$, m is 1;
$R^1$ is $CH_3$ or $CH_2CH(CH_3)_2$; provided that when $R^1$ is $CH_2CH(CH_3)_2$, then $R^2$ is 2-fluorophenyl, $R^3$ is Cl, $R^8$ is $CH_3$, U is N and V is N;
$R^2$ is 2-fluorophenyl, 2-chlorophenyl or 2-pyridyl;
$R^3$ is Cl or Br;
$R^8$ is H, $CH_3$ or $CH_2OH$;
$R^9$ is H, $CH_3$, $CH_2OH$ or $CH_2O$-t-butyl;
U is $CR^9$ or N; and
V is N or CH.

Yet another embodiment of the first aspect of the invention are compounds of formula (Ic) or pharmaceutically acceptable salts and solvates thereof wherein in each compound W is H, X is $CH_2$, n is 1, Y is $CH_2$, m is 1 and wherein $R^1$, $R^2$, $R^3$, $R^8$, U and V for each compound are as follows:

| $R^1$ | $R^2$ | $R^3$ | $R^8$ | U | V |
|---|---|---|---|---|---|
| $CH_3$ | 2-fluorophenyl | Cl | H | CH | N |
| $CH_3$ | 2-fluorophenyl | Cl | $CH_3$ | CH | N |
| $CH_3$ | 2-fluorophenyl | Cl | H | C—$CH_3$ | N |
| $CH_3$ | 2-fluorophenyl | Cl | H | C—$CH_2OH$ | N |
| $CH_3$ | 2-fluorophenyl | Cl | $CH_2OH$ | CH | N |
| $CH_3$ | 2-pyridyl | Cl | H | CH | N |
| $CH_3$ | 2-pyridyl | Cl | $CH_3$ | CH | N |
| $CH_3$ | 2-pyridyl | Br | $CH_3$ | CH | N |
| $CH_3$ | 2-pyridyl | Br | H | C—$CH_3$ | N |
| $CH_3$ | 2-pyridyl | Cl | H | C—$CH_3$ | N |
| $CH_3$ | 2-pyridyl | Cl | H | C—$CH_2OH$ | N |
| $CH_3$ | 2-pyridyl | Cl | $CH_2OH$ | CH | N |
| $CH_3$ | 2-pyridyl | Cl | $CH_3$ | C—$CH_3$ | N |
| $CH_3$ | 2-chlorophenyl | Cl | $CH_3$ | N | N |
| $CH_3$ | 2-fluorophenyl | Cl | $CH_3$ | N | N |
| $CH_2CH(CH_3)_2$ | 2-fluorophenyl | Cl | $CH_3$ | N | N |
| $CH_3$ | 2-fluorophenyl | Cl | H | N | CH |
| $CH_3$ | 2-fluorophenyl | Cl | $CH_3$ | N | CH |
| $CH_3$ | 2-fluorophenyl | Cl | H | C—$CH_2O$-t-butyl | N |
| $CH_3$ | 2-pyridyl | Cl | $CH_3$ | C—$CH_2OH$ | N |

Yet another embodiment of the first aspect of the invention are compounds of formula (1c) or pharmaceutically acceptable salts and solvates thereof wherein in each compound W is H, X is $CH_2$, n is 1, Y is $CH_2$, m is 1 and wherein $R^1$, $R^2$, $R^3$, $R^3$, U and V for each compound are as follows:

| $R^1$ | $R^2$ | $R^3$ | $R^8$ | U | V |
|---|---|---|---|---|---|
| $CH_3$ | 2-pyridyl | Br | $CH_3$ | CH | N |
| $CH_3$ | 2-pyridyl | Cl | $CH_3$ | CH | N |
| $CH_3$ | 2-fluorophenyl | Cl | $CH_3$ | N | CH |
| $CH_3$ | 2-pyridyl | Br | H | C—$CH_3$ | N |

Yet another embodiment of the first aspect of the invention is a compound of formula (Ic) or a pharmaceutically acceptable salt and solvate thereof wherein in W is H, X is $CH_2$, n is 1, Y is $CH_2$, m is 1, $R^1$ is $CH_3$, $R^2$ is 2-pyridyl, $R^3$ is Br, $R^8$ is $CH_3$, U is CH and V is N.

Those skilled in the art will recognize that a stereocenter exists in compounds of Formula (I). Accordingly, the present invention includes individual enantiomers of the compounds of Formula (I) substantially free of the other enantiomer, as well as in racemic or other admixture with the other enantiomer.

General Procedures

As used herein the symbols and conventions used in these processes, schemes and examples are consistent with those used in the contemporary scientific literature, for example, the *Journal of the American Chemical Society or the Journal of Biological Chemistry*. Standard single-letter or three-letter abbreviations are generally used to designate amino acid residues which are assumed to be in the L-configuration unless otherwise noted. Unless otherwise noted, all starting materials were obtained from commercial suppliers and used without further purification. Specifically, the following abbreviations may be used in the examples and throughout the specification: g (grams); mg (milligrams); L (liters); mL (milliliters); μL (microliters); psi (pounds per square inch); M (molar); mM (millimolar); i.v. (intravenous); Hz (Hertz); MHz (megahertz); mol (moles); mmol (millimoles); RT (room temperature); min (minutes); h (hours); mp (melting point); TLC (thin layer chromatography); HPLC (high pressure liquid chromatography); Tr (retention time); RP (reverse phase); MeOH (methanol); i-PrOH (isopropanol); TEA (triethylamine); TFA (trifluoroacetic acid); TFAA (trifluoroacetic anhydride); THF (tetrahydrofuran); DMSO (dimethylsulfoxide); EtOAc (ethyl acetate); DME (1,2-dimethoxyethane); DCM (dichloromethane); DCE (dichloroethane); DMF (N,N-dimethylformamide); DMPU (N,N'-dimethylpropyleneurea); (CDI (1,1-carbonyldiimidazole); IBCF (isobutyl chloroformate); HOAc (acetic acid); HOSu (N-hydroxysuccinimide); HOBT (1-hydroxybenzotriazole); mCPBA (meta-chloroperbenzoic acid; EDC (ethylcarbodiimide hydrochloride); BOP (bis(2-oxo-3-oxazolidinyl)phosphinic chloride); BOC (tert-butyloxycarbonyl); FMOC (9-fluorenylmethoxycarbonyl); DCC (dicyclohexylcarbodiimide); CBZ (benzyloxycarbonyl); Ac (acetyl); atm (atmosphere); TBAF (tetra-n-butylammonium fluoride); TMSE (2-(trimethylsilyl)ethyl); TMS (trimethylsilyl); TIPS (triisopropylsilyl); TBS (t-butyldimethylsilyl); DMAP (4-dimethylaminopyridine). All references to ether are to diethyl ether; brine refers to a saturated aqueous solution of NaCl. Unless otherwise indicated, all temperatures are expressed in ° C. (degrees Centigrade). All reactions conducted under an inert atmosphere at room temperature unless otherwise noted.

$^1$H NMR spectra were recorded on a Varian VXR-300, a Varian Unity-300, a Varian Unity-400 instrument, or a General Electric QE-300. Chemical shifts are expressed in parts per million (ppm, δ units). Coupling constants are in units of hertz (Hz). Splitting patterns describe apparent multiplicities and are designated as s (singlet), d (doublet), t (triplet), q (quartet), m (multiplet), br (broad).

Low-resolution mass spectra (MS) were recorded on a JOEL JMS-AX505HA, JOEL SX-102, or a SCIEX-APIiii spectrometer; high resolution MS were obtained using a JOEL SX-102A spectrometer. All mass spectra were taken under electrospray ionization (ESI), chemical ionization (CI), electron impact (EI) or by fast atom bombardment (FAB) methods. Infrared (IR) spectra were obtained on a Nicolet 510 FT-IR spectrometer using a 1-mm NaCl cell. Rotations were recorded on a Perkin-Elmer 241 polarimeter. All reactions were monitored by thin-layer chromatography on 0.25 mm E. Merck silica gel plates (60F-254), visualized with UV light, 5% ethanolic phosphomolybdic acid or p-anisaldehyde solution. Flash column chromatography was performed on silica gel (230-400 mesh, Merck). Optical rotations were obtained using a Perkin Elmer Model 241 Polarimeter. Melting points were determined using a Mel-Temp II apparatus and are uncorrected.

Compounds of general formula (I) may be prepared by methods known in the art of organic synthesis as set forth in part by the following synthesis schemes. In all of the schemes described below, it is well understood that protecting groups for sensitive or reactive groups are employed where necessary in accordance with general principles of chemistry. Protecting groups are manipulated according to standard methods of organic synthesis (T. W. Green and P. G. M. Wuts (1991) *Protecting Groups in Organic Synthesis*, John Wiley & Sons). These groups are removed at a convenient stage of the compound synthesis using methods that are readily apparent to those skilled in the art. The selection of processes as well as the reaction conditions and order of their execution shall be consistent with the preparation of compounds of Formula I. Those skilled in the art will recognize that a stereocenter exists in compounds of Formula I. Accordingly, the present invention includes both possible stereoisomers and includes not only racemic compounds but the individual enantiomers as well. When a compound is desired as a single enantiomer, it may be obtained by stereospecific synthesis or by resolution of the final product or any convenient intermediate. Resolution of the final product, an intermediate, or a starting material may be effected by any suitable method known in the art. See, for example, *Stereochemistry of Organic Compounds* by E. L. Eliel, S. H. Wilen, and L. N. Mander (Wiley-Interscience, 1994).

Compounds of Formula (Ia, wherein $X=CH_2$, $R^4=H$, $R^5$ and $R^6=O$, p=0) can be prepared according to the synthetic sequence shown in Scheme 1a and further detailed in the Examples section (vide infra). An appropriate aminobenzophenone (A) is coupled to a suitably protected (e.g., FMOC) amino acid chloride (B) in a suitable solvent, e.g., chloroform, to provide amide (C) (*J. Org. Chem.* 1986, 51, 3732-3734). Carbodiimide-mediated coupling (such as with DCC or EDC) can also be used for this condensation. Base-mediated removal of the amine protecting group (e.g., triethylamine, DCM) and subsequent cyclization (acetic acid, DCE) provides (D), which are compounds of formula Ia wherein $R^5$ and $R^6$ together represent O for compounds wherein $R^4$ is a substituent other than hydrogen, the anilide nitrogen can be alkylated by deprotonation with a base such as NaH in a suitable solvent (e.g. DMF), followed by addition of an alkylating agent such $R^4I$, thereby providing the N-alkylated compounds (E), which are also represented by formula (Ia).

SCHEME 1a

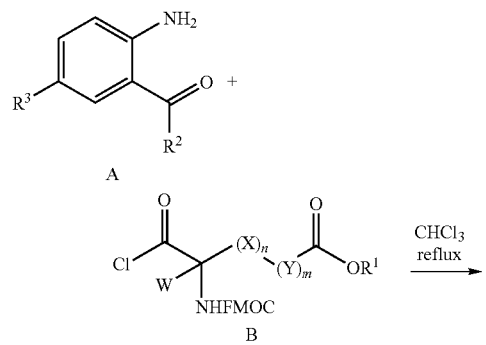

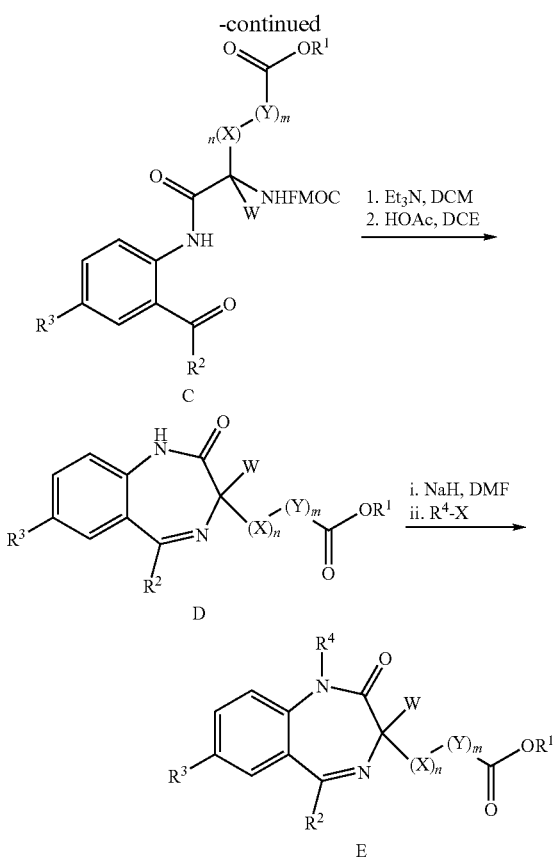

N4-oxide derivatives of compounds of Formula (I) (Z=O, p=1) can be prepared from compounds of formula (Ia) wherein p is zero according to the synthetic sequence shown in Scheme 1b. It is readily apparent to one skilled in the art that benzodiazepinones represented by structure (E) can be oxidized by treatment with mCPBA or other oxidant in a suitable solvent (e.g., DCM).

SCHEME 1b

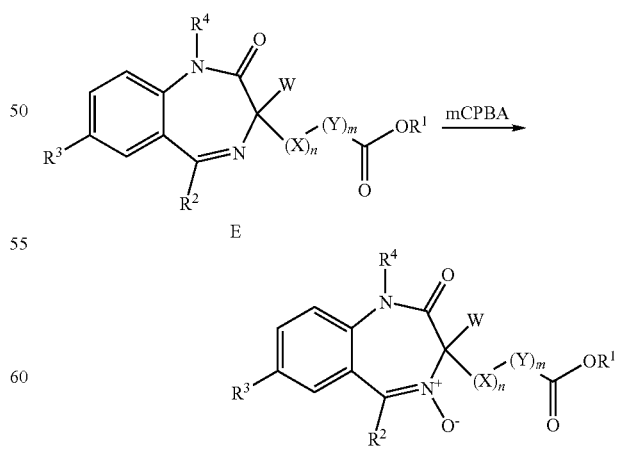

Compounds of Formula Ia wherein X is NH and p=0 may be prepared from the appropriate 3-aminobenzodiazepine F, which can be readily prepared by methods previously described (R. G. Sherrill et al., *J. Org. Chem.* 1995, 60, 730). The 3-amino-1,4-benzodiazepine thus obtained can be manipulated according to the sequence set forth in Scheme 2 and further detailed in the Examples section (vide infra). Alkylation of the 3-amino can be achieved by treatment with a 2-haloacetate (e.g. 2-bromoacetate) or conjugate addition to an appropriate unsaturated ester (e.g. methyl acrylate), providing derivatives G.

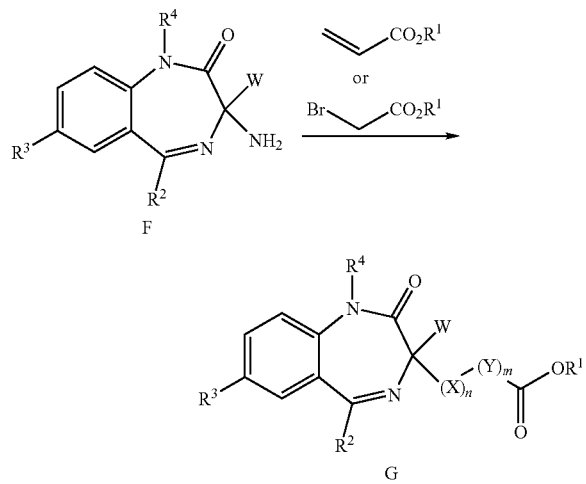

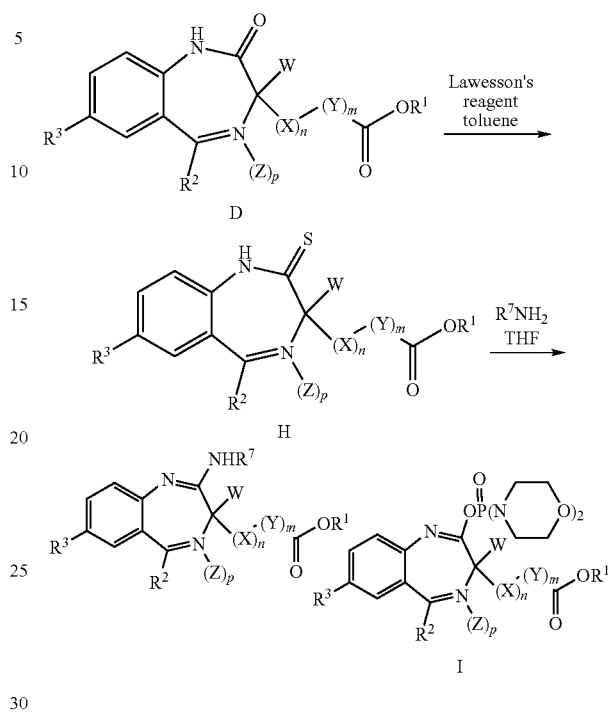

Compounds of Formula Ia (wherein $R^5R^6=O$) can be converted to their corresponding wherein $R^5R^6=S$ with Lawesson's reagent in toluene or other suitable solvent (*J. Org. Chem.* 1964, 29, 231-233).

Compounds of formula Ib may be synthesized as shown in Scheme 3 and further detailed in the Examples section (vide infra). Thus reaction of a compound of formula (1a) wherein $R^4$ is hydrogen, $R^5R^6=O$ and p is zero (D) with Lawesson's reagent as described above gives the thiolactam (H).

Condensation of the thiolactam (H) with an amine $R^7NH_2$ in tetrahydrofuran affords the corresponding compounds of Formula (1b). Alternatively, compounds of Formula (1b) can be prepared by addition of an amine $R^7NH_2$ to the iminophosphate (I) in THF, which is prepared by reaction of compound (D) with an appropriate phosphoryl chloride reagent, preferably the bis-morpholinophosphoryl chloride (Ning et al., *J. Org. Chem.* 1976, 41, 2720-2724; Ning et al., *J. Org. Chem.* 1976, 41, 2724-2727).

A method of preparation of compounds of formula (1c; $U=CR^9$; $V=N$), is set forth in Scheme 4 and further detailed in the Examples section (vide infra).

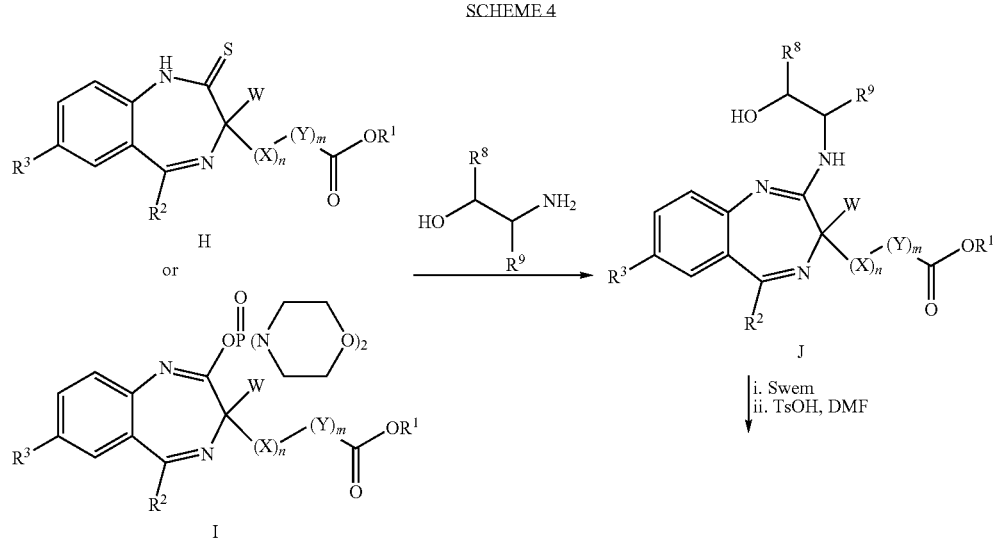

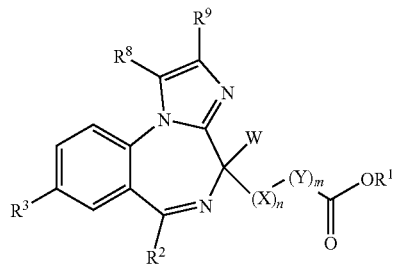

These methods are analogous to those described (WO 96/20941, WO 96/23790). Reaction between either the thiolactam (H) or iminophosphate (I) and an appropriate an amino alcohol HOCH($R^8$)—CH($R^9$)$NH_2$ provides adduct (J). Swern oxidation (i. DMSO, TFAA or (COCl)$_2$; TEA) of the hydroxyl group provides an intermediate ketone or aldehyde that undergoes cyclodehydration, spontaneously or under appropriate acidic conditions (e.g. p-toluenesulfonic acid, DMF), to provide compounds of formula (1c; U=C$R^9$; V=N).

As set forth in Scheme 5, reaction of (I) (*J. Med. Chem.* 1993, 36, 479-490; *J. Med. Chem.* 1993, 36, 1001-1006) with the anion of isonitrile ester (K) delivers imidazole (L) as the product; subsequent removal of the ester functionality by methods set forth in the examples (vide infra) provides compounds of formula 1c; U=N; V=CH).

SCHEME 5

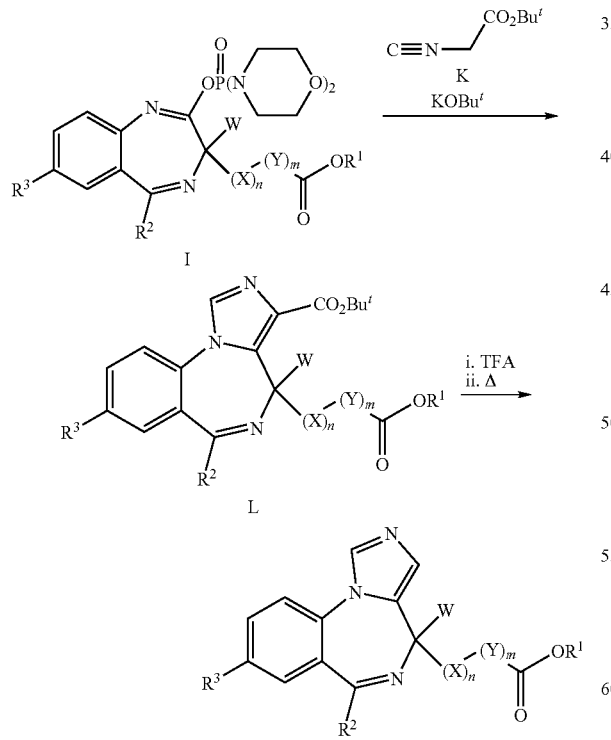

An alternative method for the preparation of compounds of formula (1c; wherein X is CH$_2$, n is Z, m=0, U=N; V=CH), is set forth in Scheme 6 and further detailed in the Examples section (vide infra). C4-unsubstituted imidazobenzodiazepine (M) is treated with a strong base (preferably potassium t-butoxide) and the anion is treated with a suitable Michael acceptor, such as t-butyl acrylate. The resultant ester adduct (N) is treated with a strong acid (e.g., TFA) to remove the t-butyl group and the carboxylic acid (O) is esterified to provide compounds of Formula (1c) by base-mediated alkylation with an alkyl halide.

SCHEME 6

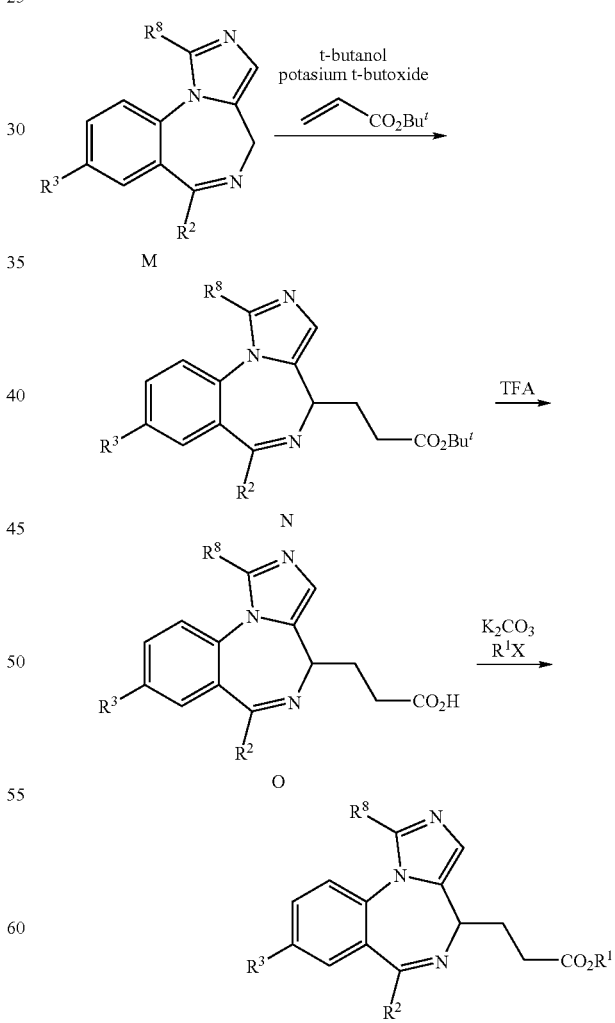

Alternative methods to prepare these compounds have also been described (e.g., *J. Org. Chem.* 1978, 43, 936-944).

Compounds of formula Ic (U=N; V=N), may be prepared as set forth in Scheme 7 and further detailed in the Examples section (vide infra). Thiolactam (H) is converted to its corresponding methylthioimidate (P), which then undergoes condensation and cyclodehydration to provide the desired triazolobenzodiazepine.

solution was stirred at room temperature for 4 h, and concentrated in vacuo to a volume of ca. 200 mL. To this stirring concentrate was added hexanes by rapid dropwise addition. The resulting slurry was stirred for 30 min and filtered to provide the required acid chloride as a white solid (83 g, 98%).

SCHEME 7

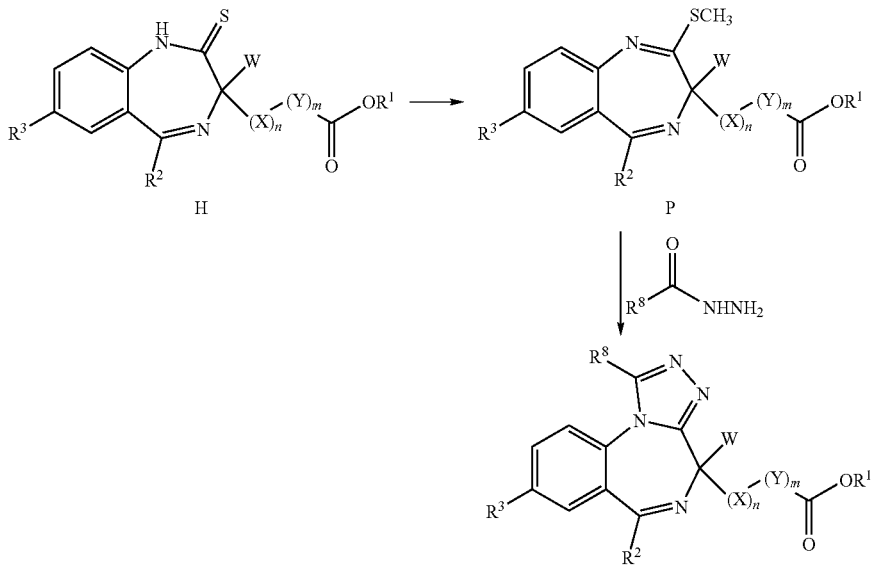

Synthesis of Key Intermediates

The following section describes the preparation of intermediates that may be used in the synthesis of compounds of Formula I. There may be examples wherein the starting material can be prepared according to the methods set forth in the synthesis of an intermediate. It should be readily apparent to one skilled in the art how these methods can be applied to include all compounds of Formula I.

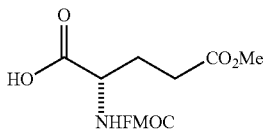

The synthesis of the FMOC-Glu(OMe)-OH was carried out as described in *Int. J. Peptide Protein Res.* 1989, 33, 353.

Intermediate-1 (Int-1)

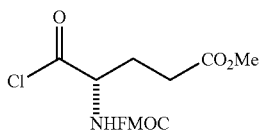

FMOC-Glu(OMe)-OH (80 g, 0.21 mol) was dissolved in $CH_2Cl_2$ (523 mL). DMF (1 mL) was added followed by dropwise addition of oxalyl chloride (19 mL, 0.22 mol). The

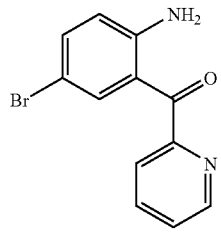

Int-2

To a −40° C. solution of 2.5 M n-butyllithium in hexane (400 mL, 1000 mmol, 4 eq) and diethyl ether (1 L) was added 2-bromopyridine (173.93 g, 1101 mmol, 4.4 eq) over approximately 30 min. The reaction was stirred for 1 h at −40° C., and then treated with 5-bromoanthranilic acid (54.14 g, 250.6 mmol, 1 eq) in THF (1 L). The reaction was warmed to 0° C. and stirred 2 h at 0° C., then quenched with chlorotrimethylsilane (625 mL, 4924 mmol, 20 eq). The reaction was stirred 30 min at ambient temperature, then cooled to 0° C. and quenched with 3N HCl (625 mL). The aqueous layer was separated, and the organic layer was extracted once with 3N HCl. The combined aqueous layers were neutralized with solid sodium hydroxide pellets, with cooling via ice bath. The resulting mixture was extracted with diethyl ether (3×1 L). The combined ether layers were dried over sodium sulfate, filtered and concentrated to a black oil, which was subsequently purified by flash chromatography (1 L silica gel, 20-30% ethyl acetate/hexane) to give the required compound as a brown solid (62 g, 224 mmol, 89.3%).

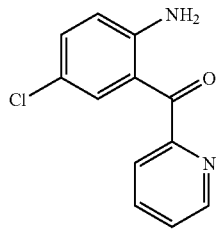

Int-3 tert-Butyllithium (43.4 mL of a 1.7 M solution in pentane, 73.8 mmol) was added to a solution of N-BOC-4-chloroaniline (7.00 g, 30.8 mmol) in THF (154 mL) at −78° C. The reaction mixture was stirred for 15 min then warmed to −20° C. and stirred an additional 2 h. The reaction mixture was cooled to −78° C., treated with 2-pyridinecarboxaldehyde (2.92 mL, 30.8 mmol), stirred for 2 h, treated with saturated aqueous NaHCO$_3$ (ca. 50 mL), and warmed to room temperature. The mixture was concentrated under reduced pressure and the residue was extracted with EtOAc (1×500 mL). The organic phase was washed with saturated aqueous NaHCO$_3$ (1×100 mL), H$_2$O (1×100 mL), saturated aqueous NaCl (1×100 mL), dried (Na$_2$SO$_4$), and concentrated under reduced pressure. The residue was dissolved in CHCl$_3$ (150 mL), treated with activated MnO$_2$ (58% by weight, 30.0 g, 200 mmol), and stirred for 18 h. The reaction mixture was filtered through a pad of Celite using additional CHCl$_3$ (ca. 100 mL) and the filtrate was concentrated under reduced pressure. Purification by flash chromatography, elution with 9:1 hexane-EtOAc, gave 6.02 g (59%) of the intermediate BOC-protected aminobenzophenone as a foam.

A solution of the BOC-protected aminobenzophenone described above (5.93 g, 17.8 mmol) and HCl (18.0 mL of a 4M solution in 1,4-dioxane, 71.3 mmol) in CH$_2$Cl$_2$ was stirred for 4 h at room temperature then concentrated under reduced pressure. The residue was diluted with EtOAc (ca. 200 mL) and treated with saturated aqueous NaHCO$_3$ until CO$_2$ evolution ceased. The layers were separated and the organic phase was washed with saturated aqueous NaHCO$_3$ (1×50 mL), H$_2$O (1×50 mL), saturated aqueous NaCl (1×50 mL), dried (Na$_2$SO$_4$), and concentrated under reduced pressure to give 3.83 g (92%) of the title compound as a yellow amorphous solid; $^1$H NMR (400 MHz, DMSO-d$_6$) δ 8.68 (d, J=4.6 Hz, 1H), 8.02 (ddd, J=7.8, 7.8, 1.6 Hz, 1H), 7.78 (d, J=7.8 Hz, 1H), 7.59 (m, 1H), 7.52 (d, J=2.6 Hz, 1H), 7.42 (br s, 2H), 7.31 (dd, J=9.0, 2.6 Hz, 1H), 6.89 (d, J=9.0 Hz, 1H); ESIMS 233 (M+H), 107 (base).

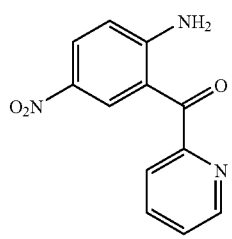

Int-4

A solution of 2-(2-aminobenzoyl)pyridine (1.29 g, 6.32 mmol, *Syn. Comm.* 1996, 26, 721-727) and trifluroacetic anhydride (1.10 mL, 7.79 mmol) in CHCl$_3$ (35 mL) was heated at 42° C. for 5 h. The reaction mixture was concentrated under reduced pressure and the residue was dissolved in EtOAc (ca. 250 mL), washed with saturated aqueous NaHCO$_3$ (2×50 mL), H$_2$O (1×50 mL), brine (1×50 mL), dried (Na$_2$SO$_4$) and concentrated under reduced pressure to give 1.91 g (99%) of the trifluoracetanilide.

A mixture of KNO$_3$ (905 mg, 8.96 mmol) in concentrated H$_2$SO$_4$ (12 mL) was added to a mixture of amide (1.76 g, 5.97 mmol) in concentrated H$_2$SO$_4$ (18 mL) maintaining the reaction temperature at ≦16° C. with an ice bath. The reaction mixture was allowed to warm to room temperature, stirred 4 h, and poured onto ice (ca. 150 g). The mixture was neutralized by slow addition of 25% aqueous NaOH (ca. 175 mL) maintaining the temperature at ≦18° C. with an ice bath. The aqueous layer was extracted with EtOAc (2×200 mL). The combined organic extracts were washed with H$_2$O (1×100 mL), brine (1×100 mL), dried (Na$_2$SO$_4$) and concentrated under reduced pressure to give a solid. Purification by flash chromatography, elution with 20% EtOAc-hexane, to provide 1.19 g (59%) of the 4-nitro-trifluoracetanilide compound as a yellow solid.

A mixture of the nitro compound prepared as above (1.14 g, 3.36 mmol), MeOH (33 mL), and H$_2$O (13 mL) was treated with K$_2$CO$_3$ (2.32 g, 16.8 mmol) and heated at reflux for 2 h. The reaction mixture was cooled to room temperature and MeOH was removed under reduced pressure. The aqueous residue was extracted with EtOAc (2×200 mL). The combined organic extracts were washed with H$_2$O (1×100 mL), brine (1×100 mL), dried (Na$_2$SO$_4$) and concentrated under reduced pressure to give Int-4, in quantitative yield, as a yellow solid.

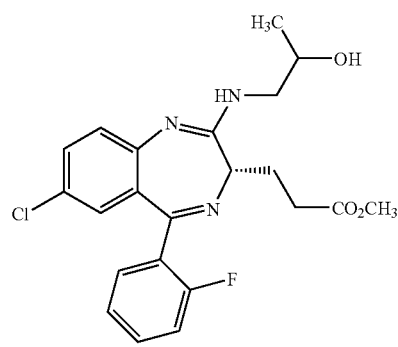

Int-5

A mixture of thiolactam (example I-28, 400 mg, 1.03 mmol), DL-1-amino-2-propanol (0.64 mL, 620 mg, 8.24 mmol) and THF (5 mL) were used according to the general procedure set forth for example 1b-1 in the Examples section. The product was purified by flash chromatography, elution with 3:7 hexane-EtOAc, to provide 300 mg (68%) of the title compound as a mixture of diastereomers: $^1$H NMR (400 MHz, CDCl$_3$) δ 7.40 (m, 2H), 7.34 (d, 1H, J=8.8 Hz), 7.17 (m, 2H), 7.07 (m, 2H), 5.62 (m, 1H), 4.02 (m, 1H), 3.68 (s, 3H), 3.27 (m, 3H), 2.79 (m, 1H), 2.44 (m, 3H), 1.20 (m, 3H).

The following intermediates were prepared according to the method set forth above:

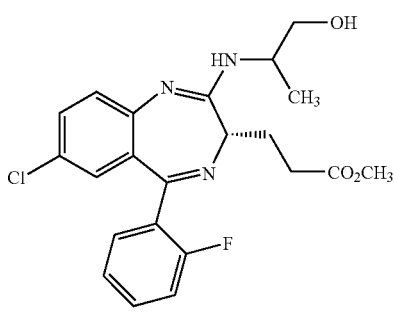
Int-6

76%; ¹H NMR (400 MHz, CDCl₃) δ 7.36 (m, 3H), 7.15 (m, 4H), 5.21 (s, 1H), 3.65 (m, 6H), 3.23 (m, 1H), 2.80 (m, 1H), 2.41 (m, 3H), 1.24 (m, 3H).

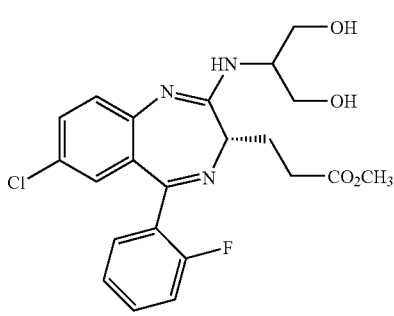
Int-7

58%; ¹H NMR (400 MHz, CDCl₃) δ 7.42 (m, 2H), 7.35 (dd, 1H, J=2.4, 8.8 Hz), 7.13 (m, 4H), 5.94 (d, 1H, J=5.6 Hz), 4.23 (br s, 1H), 3.97 (m, 1H), 3.83 (d, 2H, J=4.8 Hz), 3.68 (m, 5H), 3.28 (dd, 1H, J=3.6, 10.4 Hz), 3.08 (br s, 1H), 2.76 (m, 1H), 2.47 (m, 3H); MS (ES) m/z 448 (M⁺).

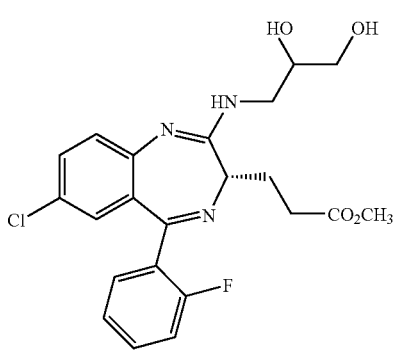
Int-8

66%; ¹H NMR (300 MHz, CDCl₃) δ 7.47 (m, 3H), 7.24 (m, 2H), 7.14 (m, 2H), 5.99 (br s, 1H), 3.81 (m, 1H), 3.72 (s, 3H), 3.62 (m, 2H), 3.53 (m, 2H), 3.30 (m, 1H), 2.80 (m, 1H), 2.50 (m, 3H); MS (CI) m/z 448 (M+H)⁺.

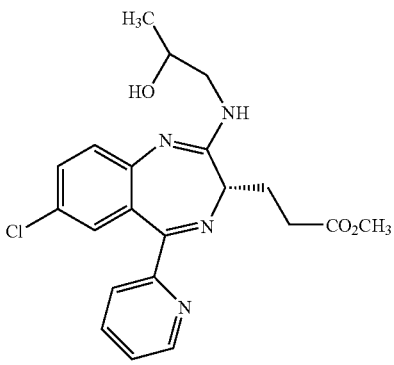
Int-9

A solution of thione (Ex. I-30, 255 mg, 0.68 mmol) and DL-1-amino-2-propanol (0.53 mL, 6.80 mmol) in THF (6 mL) was heated at reflux for 18 h, cooled to room temperature, and concentrated under reduced pressure. The residue was diluted with EtOAc (ca. 50 mL), washed with saturated aqueous NaHCO₃ (1×10 mL), H₂O (3×10 mL), saturated aqueous NaCl (1×10 mL), dried (Na₂SO₄), and concentrated under reduced pressure. Purification by flash chromatography, elution with 3:1 hexane-acetone, gave 198 mg (70%) of the amidine as a foam; ESIMS 415 (M+H, base).

The following intermediates were prepared according to the method set forth above:

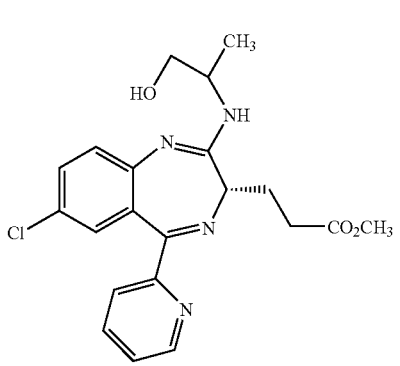
Int-10

36%; ESIMS 415 (M+H, base).

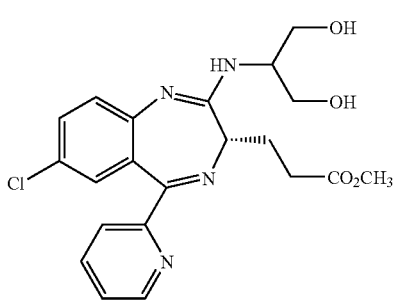
Int-11

38%; MS (ESI) m/z 430 (M⁺).

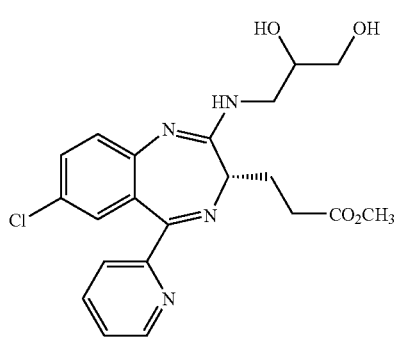

Int-12

35%; MS (ESI) m/z 430 (M+).

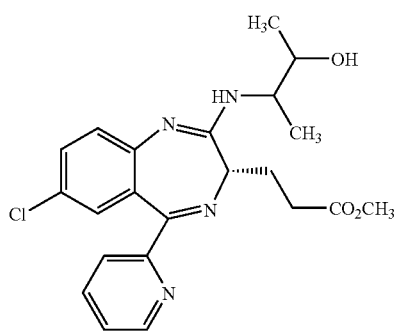

Int-13

Condensed with 3-amino-2-butanol (*J. Org. Chem.* 1977, 42, 3541) 56% (mixture of diastereomers); $^1$H NMR (300 MHz, CDCl$_3$) δ 8.65 (d, 1H, J=4.5 Hz), 7.81 (m, 2H), 7.34 (m, 2H), 7.18 (m, 2H), 5.30 (m, 1H), 3.90 (m, 1H), 3.76 (m, 1H), 3.70 (m, 3H), 3.32 (m, 1H), 2.77 (m, 1H), 2.50 (m, 3H), 1.24 (m, 3H), 1.24 (m, 3H), 1.11 (m, 3H); MS (ES) m/z 428 (M+).

Int-14

27%; $^1$H NMR (400 MHz, DMSO-d$_6$) δ 8.52 (d, 1H, J=4.8 Hz), 7.91 (m, 2H), 7.45 (t, 1H, J=6 Hz), 7.36 (dd, 1H, J=2.4, 8.8 Hz), 7.08 (m, 3H), 4.73 (t, 1H, J=5.6 Hz), 3.57 (s, 3H), 3.48 (m, 2H), 3.18 (m, 2H), 2.5 (m, 2H), 2.24 (m, 2H); MS (ESI) m/z 401 (M+).

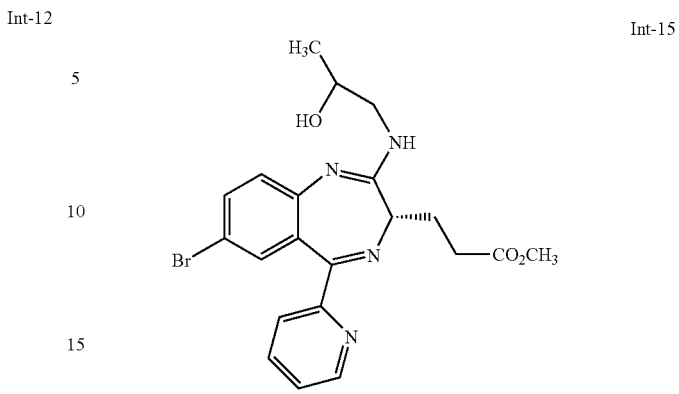

Int-15

A solution of the lactam (Ex. I-10, 7.31 g, 18.2 mmol) in THF (21 mL) was added to a suspension of NaH (870 mg of 60% oil dispersion, 21.8 mmol) in THF (70 mL) at 0° C. The reaction mixture was stirred at 0° C. for 30 min, warmed to room temperature and stirred for 30 min, then cooled to 0° C.

(Dimorpholino)phosphorochloridate (6.48 g, 25.5 mmol) was added, the mixture was allowed to warm to room temperature over 4.5 h, and the mixture was filtered with additional THF (ca. 10 mL). A mixture of the filtrate and DL-1-amino-2-propanol (2.80 mL, 36.4 mmol) was stirred at room temperature for 18 h and concentrated under reduced pressure. The residue was diluted with EtOAc (ca. 250 mL), washed with saturated aqueous NaHCO$_3$ (1×75 mL), H$_2$O (2×75 mL), saturated aqueous NaCl (1×75 mL), dried (Na$_2$SO$_4$), and concentrated under reduced pressure. Purification by flash chromatography, elution with 19:1 EtOAc-MeOH, gave 3.06 g (37%) of Int-15 as a foam; ESIMS 459 (M+H, base).

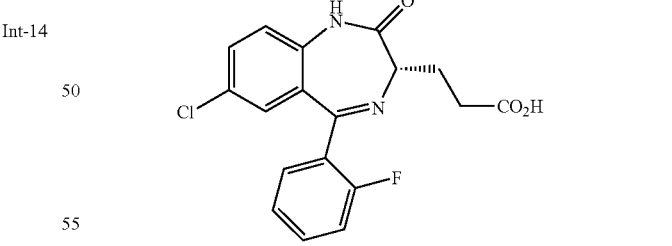

Int-16

Benzodiazepinone I-1 (510 mg) was dissolved in dioxane (6 mL) and cooled to 0° C. To this was added 4 mL 1M aqueous LiOH. The mixture was stirred at 0° C. until TLC indicated complete reaction. The mixture was acidified with 1 M H$_3$PO$_4$ and extracted with ethyl acetate (3×). The combined organic layers were washed with brine, dried over magnesium sulfate, filtered, and concentrated under reduced pressure to afford Int-16 as a tan powder (400 mg).

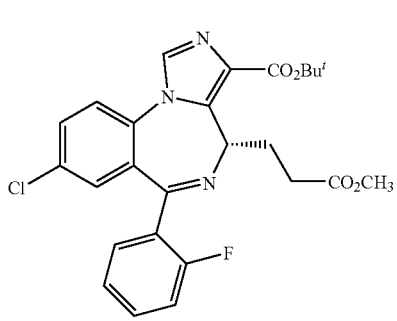

Int-17

In a dry flask under nitrogen atmosphere was placed DMF (60 mL), tert-butylisocyanoacetate (0.69 mL, 4.5 mmol) and iminophosphate (Int-19, 1.44 g, 2.82 mmol). The contents were cooled to 0° C. and then treated with potassium tert-butoxide (0.532 g, 4.50 mmol). The resulting purple solution was stirred at 0° C. for thirty minutes then poured into a flask containing 100 mL of a 5% acetic acid solution. The aqueous layer was extracted with ethyl acetate and the extracts were washed three times with water. The organics were dried over magnesium sulfate, filtered and concentrated. The residue was purified by flash chromatography through silica gel to yield Int-17 (1.35 g, 2.70 mmol) in 95% yield. $^1$H NMR (CDCl$_3$): 7.90(s, 1H), 7.50-7.60(m, 3H), 7.44(m, 1H), 7.20-7.26(m, 2H), 7.03(t, 1H, J=9.3 Hz), 6.50(dd, 1H, J=6.7, 9.3 Hz), 3.55(s, 3H), 2.32-2.46(m, 2H), 1.85-2.00(m, 2H), 1.60 (s, 9H). MS(ES+)=498(10%, M+), 520(80%, M+22).

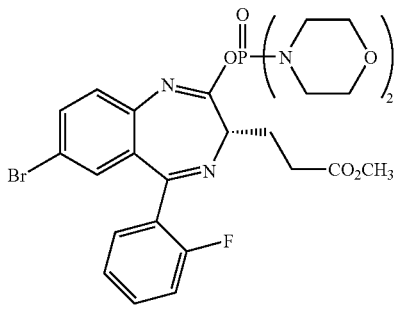

Int-18

Benzodiazepinone I-3 (1.25 g, 3.0 mmol) was added to a suspension of NaH (3.3 mmol) in THF (10 mL). The resulting solution was stirred for 10 min and bis-morpholinophosphorochloridate (762 mg, 3.0 mmol; Ning et al., *J. Org. Chem.* 1976, 41, 2720-2724) was added. After 1 h an additional 100 mg of the phosphoryl chloride was added. The mixture was stirred for 1 h and filtered. The filtrate was concentrated and the residue was chromatographed on silica gel (graded elution with 4:1 CH$_2$Cl$_2$:ether and 8:1:1 CH$_2$Cl$_2$:ethyl acetate: methanol) to afford 1.3 g of the iminophosphate Int-18 as a white foam.

Int-19

The following intermediate was prepared according to the method set forth above in Int-18, using Example I-1 as the starting benzodiazepinone:

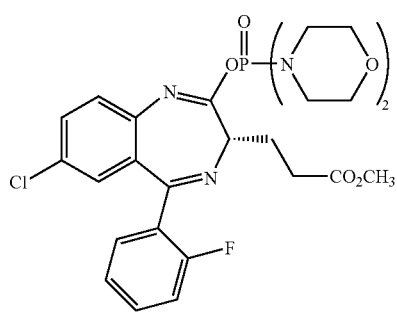

Synthesis of Compounds of Formula Ia

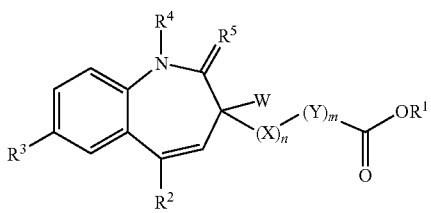
(1a)

EXAMPLE I-1

Methyl 3-[(3S)-7-chloro-5-(2-fluorophenyl)-2-oxo-2,3-dihydro-1H-1,4-benzodiazepin-3-yl]propanoate

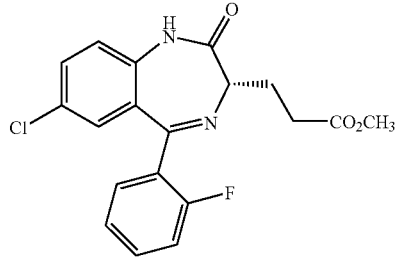

A mixture of 2-amino-5-chloro-2'-fluorobenzophenone (24.9 g, 99.7 mmol), the acid chloride (Int-1, 41.7 g, 104 mmol), and CHCl$_3$ (100 mL) were heated at reflux for 30 min and then allowed to cool to RT. Ether (600 mL) was added causing a precipitate to form. The reaction mixture was cooled to 0° C. for 15 min, and the solid was collected and washed with additional portions of ether. The solid was dried in vacuo to provide 55.4 g (90%) of amide. $^1$H NMR (CDCl$_3$, 300 MHz) δ 8.70 (d, 2H, J=9.2 Hz), 7.74 (d, 2H, J=11.2 Hz), 7.62 (m, 4H), 7.46 (s, 1H), 7.37 (m, 2H), 7.26 (m, 3H), 7.17 (m, 1H), 5.80 (d, 1H, J=6 Hz), 4.48 (m, 2H), 4.34 (m, 1H), 4.24 (m, 1H), 3.68 (s, 3H), 2.55 (m, 3H), 2.14 (m, 1H).

A mixture of the amide (42 g, 68 mmol) and Et$_3$N (170 mL) in CH$_2$Cl$_2$ (170 mL) was stirred at 40° C. overnight. The reaction mixture was concentrated under reduced pressure and the residue was dried in vacuo for 5 min to provide an oil. To this oil were added HOAc (35 mL) and 1,2-dichloroethane (665 mL) and the mixture was stirred at 40° C. overnight. The reaction mixture was concentrated under reduced pressure and the residue was dissolved in CH$_2$Cl$_2$, slurried onto silica gel and dried to a free-flowing powder. The silica gel was washed with several portions of hexane, which were discarded, and then with several portions of 9:1 CH$_2$Cl$_2$:CH$_3$OH. The CH$_2$Cl$_2$/CH$_3$OH washings were combined and concentrated under reduced pressure to provide an oil. Ether was added to the oil to give a white solid which was filtered, washed with several additional portions of ether and dried in vacuo to provide 14 g (55%) of the title compound. $^1$H NMR (300 MHz, CDCl$_3$) δ 8.94 (br s, 1H), 7.54 (m, 1H), 7.45 (m, 1H), 7.23 (m, 1H), 7.20 (d, 1H, J=2.4 Hz), 7.12 (d, 1H, J=8.8 Hz), 7.06 (m, 1H), 3.67 (m, 4H), 2.68 (m, 2H), 2.60 (m, 1H), 2.51 (m, 1H).

The following compounds were prepared according to the general procedure set forth above in Example I-1. Any modifications in starting materials or conditions that are required for the synthesis of a particular example will be readily apparent to one skilled in the art of organic synthesis. For example, in the synthesis of the compound of example I-2, it should be readily apparent that the amino acid chloride required for the synthesis derives from L-aspartic acid.

EXAMPLE I-2

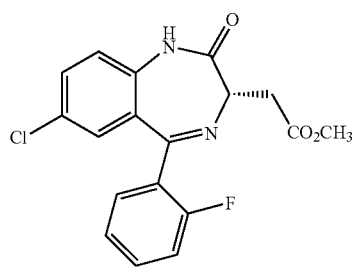

$^1$H NMR (300 MHz, DMSO) δ 11.0 (bs, 1H), 4.05 (t, 1H), 3.7 (s, 3H). MS (ES+): 361 (M+1)$^+$.

EXAMPLE I-3

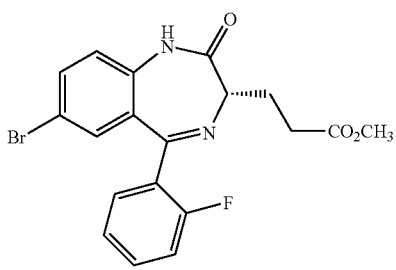

$^1$H NMR (400 MHz, CDCl$_3$) δ 8.74 (bs, 1H), 7.61-7.43 (m, 3H), 3.67 (s, 3H), 2.70-2.49 (m, 4H).

EXAMPLE I-4

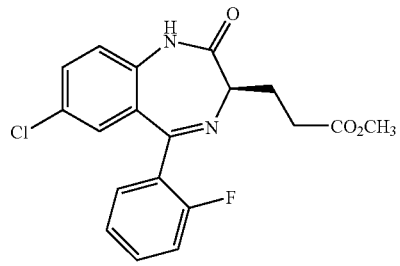

$^1$H NMR (400 MHz, CDCl$_3$) δ 9.08 (bs, 1H), 7.58-7.03 (m, 7H), 3.67 (s, 3H), 2.74-2.44 (m, 4H).

EXAMPLE I-5

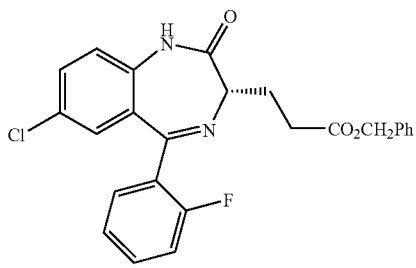

$^1$H NMR (400 MHz, DMSO-d$_6$) δ 10.78 (bs, 1H), 5.04 (s, 2H), 3.55 (m, 1H)

EXAMPLE I-6

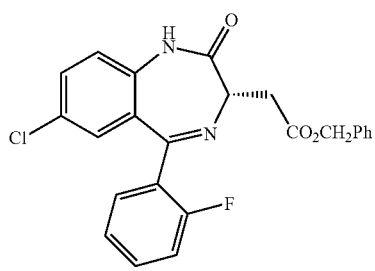

$^1$H NMR (400 MHz, DMSO) δ 10.9 (bs, 1H), 5.1 (s, 2H), 4.05 (t, 1H). MS (ES+): 437 (M+1)$^+$.

EXAMPLE I-7

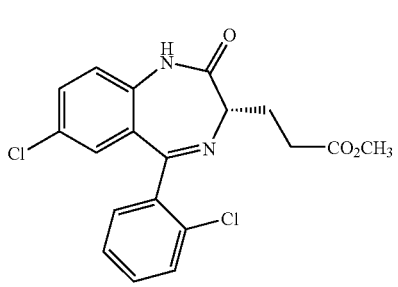

$^1$H NMR (300 MHz, CDCl$_3$) δ 9.04 (bs, 1H), 3.72 (m, 1H), 3.66 (s, 3H). MS (ES): 391 (M+1)$^+$.

EXAMPLE I-8

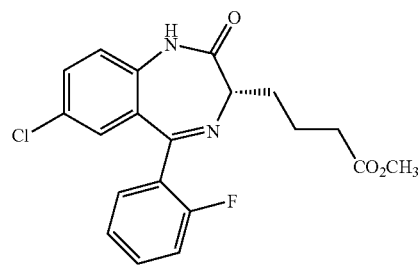

$^1$H NMR (300 MHz, CDCl$_3$) δ 8.5 (bs, 1H), 3.7 (s, 3H), 3.6 (m, 1H). MS (ES): 389 (M+1)$^+$.

EXAMPLE I-9

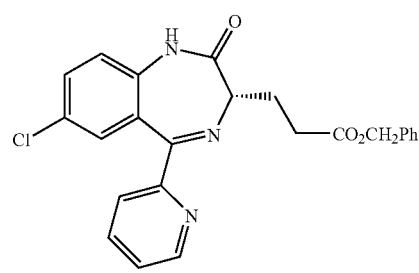

$^1$H NMR (400 MHz, CDCl$_3$) δ 8.59 (d, J=4.6 Hz, 1H), 8.07 (d, J=7.9 Hz, 1H), 7.80 (comp, 2H), 7.46 (dd, J=8.6, 2.4 Hz, 1H), 7.35 (m, 2H), 7.30 (comp, 5H), 7.01 (d, J=8.6 Hz, 1H), 5.10 (s, 2H), 3.75 (dd, J=5.8, 4.0 Hz, 1H), 2.73 (dd, J=7.1 Hz, 2H), 2.56 (m, 2H); ESIMS 456 (M+Na), 434 (M+H, base); Anal. Calcd. for C$_{24}$H$_{20}$ClN$_3$O$_3$·0.25H$_2$O: C, 65.75; H, 4.71; N, 9.59. Found: C, 65.65; H, 4.96; N, 9.19.

EXAMPLE I-10

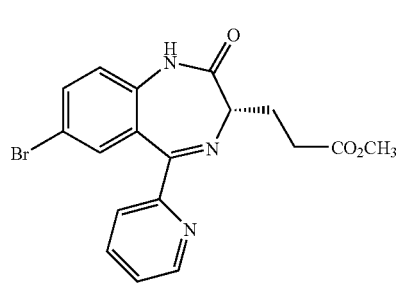

$^1$H NMR (400 MHz, CDCl$_3$) δ 8.60 (d, J=4.6 Hz, 1H), 8.09 (comp, 2H), 7.82 (ddd, J=7.8, 7.8, 1.3 Hz, 1H), 7.60 (dd, J=8.6, 2.2 Hz, 1H), 7.53 (d, J=2.2 Hz, 1H), 7.37 (dd, J=7.2, 5.0 Hz, 1H), 6.98 (d, J=8.6 Hz, 1H), 3.76 (dd, J=7.5, 5.9 Hz, 1H), 3.67 (s, 3H), 2.67 (m, 2H), 2.56 (m, 2H); ESIMS 424 (M+Na), 402 (M+H, base).

EXAMPLE I-11

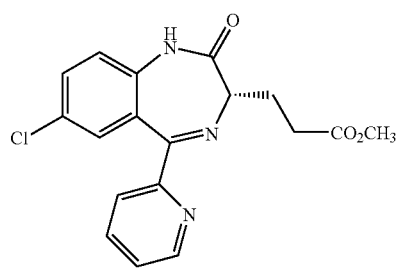

38%; $^1$H NMR (400 MHz, CDCl$_3$) δ 8.58 (d, J=4.6 Hz, 1H), 8.07 (d, J=7.8 Hz, 1H), 7.94 (s, 1H), 7.80 (ddd, J=7.8, 7.8, 1.6 Hz, 1H), 7.52 (dd, J=8.6, 2.4 Hz, 1H), 7.37 (m, 2H), 7.02 (d, J=8.6 Hz, 1H), 3.75 (dd, J=7.6, 5.6 Hz, 1H), 3.65 (s, 3H), 2.66 (m, 2), 2.53 (m, 2H).

EXAMPLE I-12

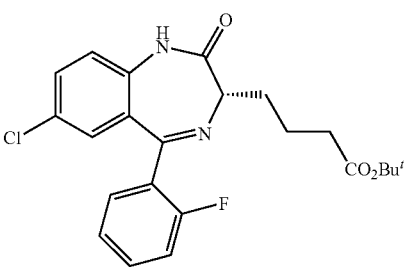

$^1$H NMR (300 MHz, CDCl$_3$) δ 9.0 (bs, 1H), 3.6 (m, 1H), 1.4 (s, 9H). MS (ES): 431 (M+1)$^+$.

EXAMPLE I-13

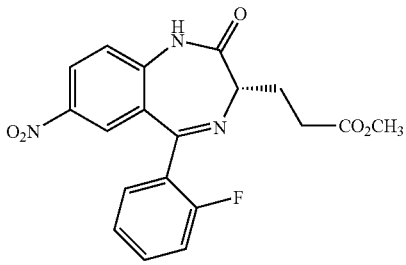

Nitronium tetrafluoroborate (4.85 mL of a 0.5 M solution in sulfolane, 2.43 mmol) was added to a solution of the A-ring unsubstituted benzodiazepine (501 mg, 1.47 mmol) in $CH_3CN$ (7.4 mL) at 0° C. The reaction mixture was allowed to warm to RT overnight and quenched by addition of $H_2O$. The reaction mixture was diluted with EtOAc, washed with saturated aqueous $NaHCO_3$, $H_2O$, brine, dried ($Na_2SO_4$), and concentrated under reduced pressure to give an oil. Purification by flash chromatography, elution with 55:45 hexane-EtOAc, provided the product in sulfolane. This material was partitioned between ether and $H_2O$, the layers were separated, and the aqueous layer was extracted with ether. The combined ether layers were washed with $H_2O$ (3×), brine, dried ($MgSO_4$) and concentrated to provide the title compound as a yellow solid. $^1H$ NMR (400 MHz, DMSO-$d_6$) δ 11.31 (s, 1H), 7.92 (d, 1H), 7.65-7.55 (m, 2H), 3.57 (s, 3H), 2.63-2.17 (m, 4). MS (AP+) calcd. MH+386, found 386; (AP−) calcd. [M−H]−384, found 384.

EXAMPLE I-14

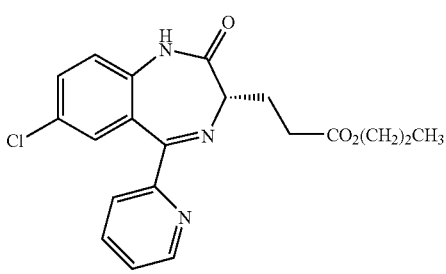

Example I-14 was prepared from the corresponding methyl ester (Example I-11) using the following transesterification procedure (Otera, J. et al. *J. Org. Chem.* 1991, 56, 5307):

A mixture of the methyl ester (1 eq.), propyl alcohol (4-5 eq.), and bis(dibutylchlorotin) oxide (0.1 eq.) in $PhCH_3$ (0.1 M) was heated at reflux until the reaction was judged complete by TLC. The reaction mixture was allowed to cool to room temperature and was concentrated under reduced pressure. Purification by flash chromatography, elution with hexane-EtOAc, delivered the desired propyl ester (90%). ESIMS 408 (M+Na, base), 386 (M+H); Anal. Calcd. for $C_{20}H_{20}ClN_3O_3$: C, 62.26; H, 5.22; N, 10.89. Found: C, 62.00; H, 5.32; N, 10.69.

The following compounds were prepared according to the general procedure set forth above in example I-14, using the appropriate methyl ester as the starting material.

EXAMPLE I-15

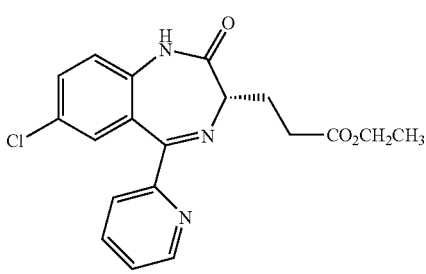

66%; ESIMS 394 (M+Na, base), 372 (M+H); Anal. Calcd. for $C_{21}H_{22}ClN_3O_3$— 0.25$H_2O$: C, 60.64; H, 4.96; N, 11.17. Found: C, 60.54; H, 5.01; N, 10.96.

EXAMPLE I-16

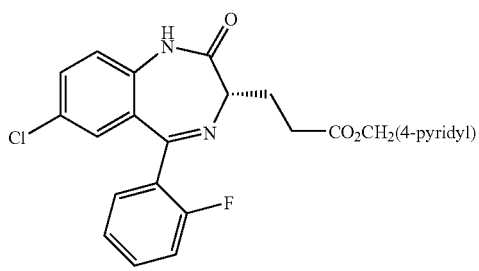

$^1H$ NMR (CDCl$_3$, 400 MHz) δ 8.85 (bs, 1H), 8.57 (d, 2H), 5.13 (s, 2H).

EXAMPLE I-17

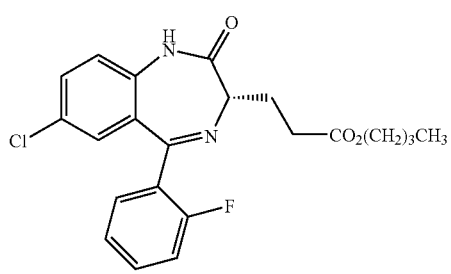

$^1H$ NMR (CDCl$_3$, 400 MHz) δ 8.38 (bs, 1H), 4.05 (t, 2H), 1.37-1.32 (m, 2H), 0.89 (t, 3H). ESIMS 439 (M+Na), 417 (M+H, base).

EXAMPLE I-18

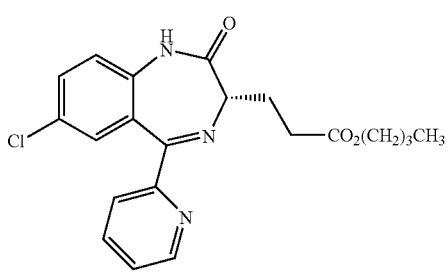

91%; ESIMS 422 (M+Na, base), 400 (M+H); Anal. Calcd. for $C_{21}H_{22}ClN_3O_3$: C, 63.08; H, 5.55; N, 10.51. Found: C, 62.83; H, 5.59; N, 10.44.

EXAMPLE I-19

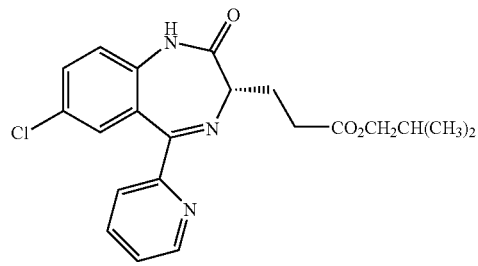

88%; ESIMS 422 (M+Na, base), 400 (M+H); Anal. Calcd. for $C_{21}H_{22}ClN_3O_3$: C, 63.08; H, 5.55; N, 10.51. Found: C, 62.82; H, 5.65; N, 10.36.

EXAMPLE I-20

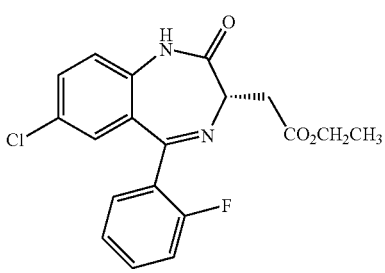

Prepared by Fisher esterification (ethanol, TFA) of the corresponding carboxylic acid (Int-16). $^1$H NMR (400 MHz, $CDCl_3$) δ 8.54 (bs, 1H), 4.2 (m, 3H), 1.3 (t, 3H).

EXAMPLE I-21

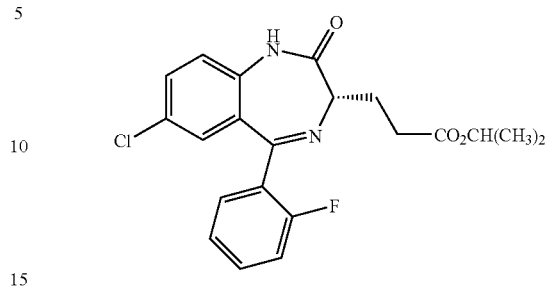

Prepared by Fisher esterification (2-propanol, trace conc. $H_2SO_4$) of the corresponding carboxylic acid (Int-16). ESIMS 403 (M+H, base).

EXAMPLE I-22

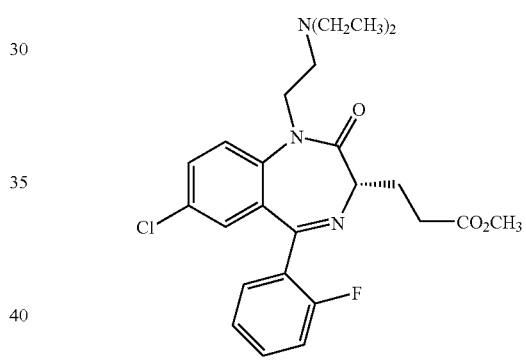

Benzodiazepine I-1 (308 mg, 0.82 mmol) was added to a stirring suspension of NaH (39 mg, 0.98 mmol) in DMF (8 mL). The resulting mixture was heated to 70° C. for 15 min at which time a homogeneous solution formed. To this solution was added 2-chloroethyl-diethylamine (270 mg, 1.6 mmol). The resulting solution was stirred for 30 min and partitioned between ethyl acetate and $H_2O$. The organic phase was washed with saturated $H_2O$ and saturated aq NaCl, dried ($Na_2SO_4$), and concentrated under reduced pressure. Silica gel chromatography (95:5, chloroform:methanol) provided the desired compound as a yellow oil (88%). $^1$H NMR ($CDCl_3$, 400 MHz) δ 4.39-4.31 (m, 1H), 3.64 (s, 3H), 0.99 (t, 6H). ESIMS 474 (M+H, base).

The following compounds were prepared according to the general procedure set forth above in Example I-22. Any modifications in starting materials or conditions that are required for the synthesis of a particular example will be readily apparent to one skilled in the art of organic synthesis.

EXAMPLE I-23

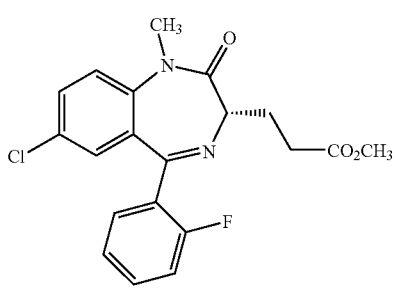

$^1$H NMR (CDCl$_3$, 400 MHz) δ 3.65 (s, 3H), 3.43 (s, 3H).

EXAMPLE I-24

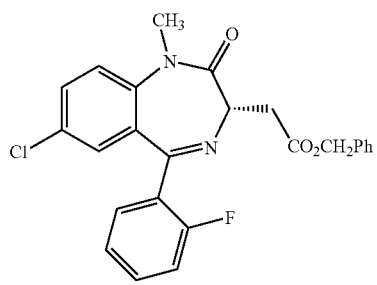

$^1$H NMR (CDCl$_3$, 400 MHz) δ 5.21-5.11 (dd, 2H), 4.14 (t, 1H), 3.41 (s, 3H).

EXAMPLE I-25

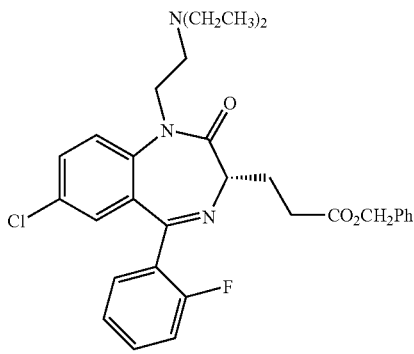

$^1$H NMR (CDCl$_3$, 400 MHz) δ 5.07 (s, 2H), 4.37-4.30 (m, 1H), 3.77 (m, 1H), 3.64 (m, 1H). ESIMS 550 (M+H, base).

EXAMPLE I-26

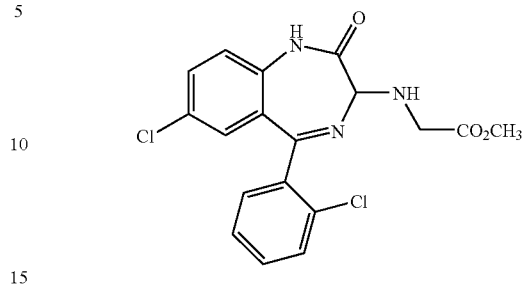

The 3-amino-benzodiazepine (*J. Med. Chem.* 1968, 11, 457; 0.15 g, 0.47 mmol) and DMF (4 mL) were added to a round-bottom flask and cooled to 0° C. Triethylamine (0.07 mL, 0.05 g, 0.52 mmol) was added to the reaction mixture followed by dropwise addition of methyl bromoacetate (0.04 mL, 0.07 g, 0.47 mmol). The reaction was allowed to warm to RT over 4 h. When the reaction was judged to be complete, the mixture was poured into a separatory funnel containing ethyl acetate and water. The organic layer was collected and was washed with water, saturated aqueous brine, dried over Na$_2$SO$_4$, filtered and concentrated under reduced pressure. The product was isolated by flash chromatography using 4:1 ethyl acetate/hexanes as eluant to provide compound I-26 as white solid (57%). $^1$H NMR (300 MHz, DMSO-d$_6$) δ 11.0 (s, 1H), 7.59 (m, 5H), 7.29 (d, 1H, J=9 Hz), 6.98 (d, 1H, J=2.4 Hz), 4.41 (s, 1H), 3.65 (m, 2H), 3.63 (s, 3H), 3.22 (bs, 1H). MS (ES): 392 (M$^+$).

EXAMPLE I-27

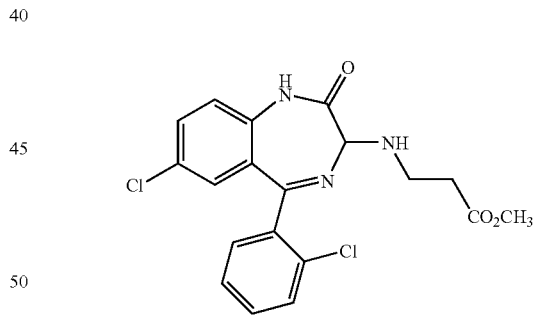

The 3-amino-benzodiazepine (*J. Med. Chem.* 1968, 11, 457; 0.15 g, 0.47 mmol) and ethanol (3 mL) were combined in a round bottom flask. Methyl acrylate (0.05 mL, 0.05 g, 0.52 mmol) was added and the reaction mixture stirred for 5 d at 20° C. The reaction mixture was poured into a separatory funnel containing ethyl acetate and water. The organic layer was collected and was washed with water, saturated aqueous brine, dried over Na$_2$SO$_4$, filtered and concentrated under reduced pressure. The product was isolated by flash chromatography using 4:1 ethyl acetate/hexanes as eluant to provide I-27 as white solid (12%). $^1$H NMR (400 MHz, DMSO-d$_6$) δ 10.88 (s, 1H), 7.58 (dd, 1H, J=2.4, 8.8 Hz), 7.49 (m, 4H), 7.22

(d, 1H, J=8.8 Hz), 6.93 (d, 1H, J=2.4 Hz), 4.23 (s, 1H), 3.54 (s, 3H), 3.09 (bs, 1H), 2.86 (bs, 2H), 2.60 (m, 1H). MS (ES): 406 (M+).

EXAMPLE I-28

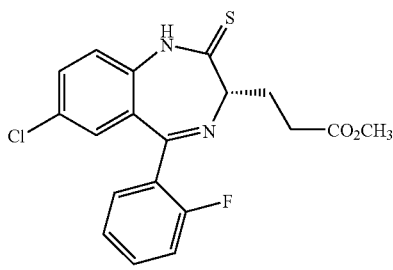

A suspension of the benzodiazepinone (Example I-1, 16.95 g, 45.32 mmol), Lawesson's reagent (21.97 g, 54.32 mmol) and PhCH$_3$ (200 mL) was heated at 100° C. After 30 min, the reaction became homogeneous, was judged to be complete and was allowed to cool to RT causing a precipitate to form. Ether (400 mL) was added, causing additional precipitate to form, and the mixture was filtered. Silica gel was added to the filtrate and this mixture was concentrated under reduced pressure to give a free-flowing powder. The silica gel was slurried in CH$_2$Cl$_2$, filtered, and the filtrate was concentrated under reduced pressure to give a yellow viscous oil. Ether was added to the oil to precipitate a pale yellow solid that was filtered, washed with several additional portions of ether, and dried in vacuo to provide 11.47 g (65%) of I-28 as a yellow solid. $^1$H NMR (CDCl$_3$, 300 MHz) δ 10.1 (br s, 1H), 7.60 (t, 1H, J=7.4 Hz), 7.51 (m, 2H), 7.21 (m, 2H), 7.19 (d, 1H, J=8.4 Hz), 7.15 (t, 1H, J=9.3 Hz), 3.95 (m, 1H), 3.69 (s, 3H), 2.86 (m, 1H), 2.68 (m, 3H).

The following example was prepared according to the procedure set forth above in example I-28:

EXAMPLE I-29

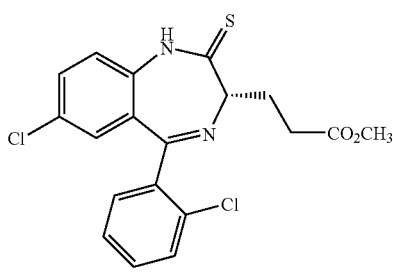

MS (ES): 408 (M+1)+.

EXAMPLE I-30

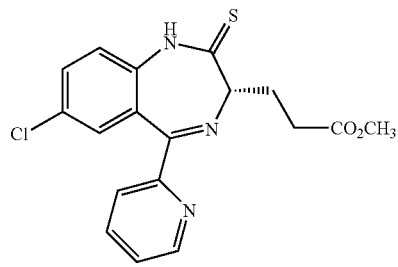

A mixture of benzodiazepinone Ex I-11 (1.00 g, 2.80 mmol) and Lawesson's reagent (1.13 g, 2.80 mmol) in PhCH$_3$ (19 ml) was heated at reflux for 2 h, cooled to room temperature, and concentrated under reduced pressure. The residue was purified immediately by flash chromatography, elution with 50:1 CH$_2$Cl$_2$:MeOH, to give 260 mg (25%) of thione as a foam; $^1$H NMR (400 MHz, DMSO-d$_6$) δ 12.58 (s, 1H), 8.55 (d, J=4.4 Hz, 1H), 8.03 (d, J=7.9 Hz, 1H), 7.95 (m, 1H), 7.65 (dd, J=8.8, 2.4 Hz, 1H), 7.51 (dd, J=6.4, 5.0 Hz, 1H), 7.37 (comp, 2H), 3.83 (m, 1H), 3.58 (s, 3H), 2.52 (m, 4H).

EXAMPLE I-31

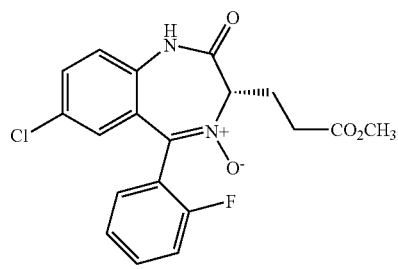

Benzodiazepinone Ex I-1 (374 mg, 1 mmol) was dissolved in CH$_2$Cl$_2$ (7 mL). To this was added mCPBA (393 mg, 2.3 mmol) in one portion. The mixture was stirred for 18 h, diluted with CH$_2$Cl$_2$ (50 mL), washed with sat NaHCO$_3$ and brine. The organic layer was dried over magnesium sulfate, filtered, and concentrated. The residue was purified immediately by flash chromatography, elution with 95:5 CH$_2$Cl$_2$:MeOH, to give 289 mg of the N-oxide as a white solid (74%). $^1$H NMR NMR (CDCl$_3$, 400 MHz) δ 9.02 (br s, 1H), 4.50 (m, 1H). ESIMS 413 (M+Na, base).

Synthesis of Compounds of Formula Ib

Compounds of formula (1b) may be prepared from the corresponding thiolactam of formula (1a) wherein R$^4$ is hydrogen and R$^5$, R$^6$=S) by the following general methods.

General Procedure 1: the Addition of Amines to Thiolactam to Produce Amidines.

The Thiolactam, the appropriate amine (5-20 mmol/mmol of thiolactam), and either tetrahydrofuran (THF, 2-10 mL/mmol of thiolactam) or 1,4-dioxane (dioxane, 2-10 mL/mmol of thiolactam) were combined and heated to 50° C. (THF) or 95° C. (dioxane) for 2-72 h. When the reaction was judged by TLC to be complete, the reaction mixture was allowed to cool to RT. The solvents were removed in vacuo and, in some cases, the residue was directly chromatographed on silica gel to provide the desired amidine. In other cases, the remaining residue was dissolved in an appropriate solvent (EtOAc, for example) and the product was washed with H$_2$O, brine, dried (MgSO$_4$ or CaSO$_4$), filtered and the solvents were again removed under reduced pressure and the residue was chromatographed on silica gel to provide the desired amidine of Formula Ib.

The following compounds were prepared according to the general procedure above. Any modifications in starting materials or conditions that are required for the synthesis of a particular example will be readily apparent to one skilled in the art of organic synthesis.

EXAMPLE Ib-1

Methyl 3-[(3S)-7-chloro-5-(2-fluorophenyl)-2-(methylamino)-3H-1,4-benzodiazepin-3-yl]propanoate

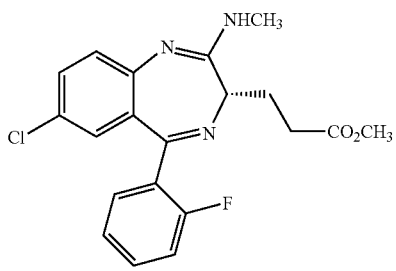

$^1$H NMR (400 MHz, CDCl$_3$) δ 7.43-7.05 (m, 7H), 5.20 (bs, 1H), 3.68 (s, 3H), 2.87 (d, 3H), 2.51-2.30 (m, 3H). MS (ESI) m/z 388 (M+H)$^+$, base.

EXAMPLE Ib-2

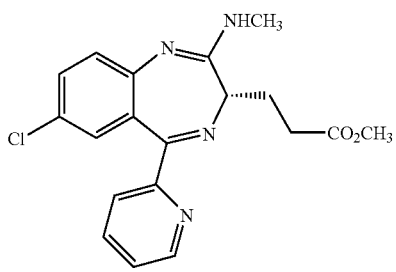

$^1$H NMR (400 MHz, CDCl$_3$) δ 8.82 (d, 1H), 8.43 (t, 1H), 8.14 (d, 1H), 7.97 (m, 1H), 7.80 (dd, 1H), 7.64 (m, 2H), 4.17 (dd, 1H), 3.65 (s, 3H), 3.14 (s, 3H), 2.84-2.36 (m, 4H). MS (AP+) m/z 371 (M+H)$^+$.

EXAMPLE Ib-3

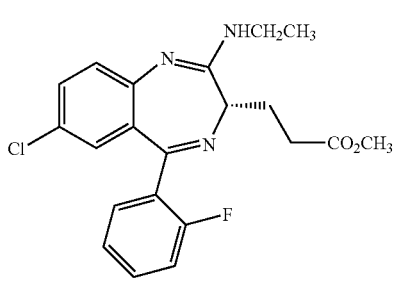

23%; $^1$H NMR (400 MHz, CDCl$_3$) δ 7.52-7.06 (m, 7H), 5.00 (bs, 1H), 3.70 (s, 3H), 3.52-3.22 (m, 3H), 2.80 (m, 1H), 2.57-2.33 (m, 3H), 1.21 (t, 3H).

EXAMPLE Ib-4

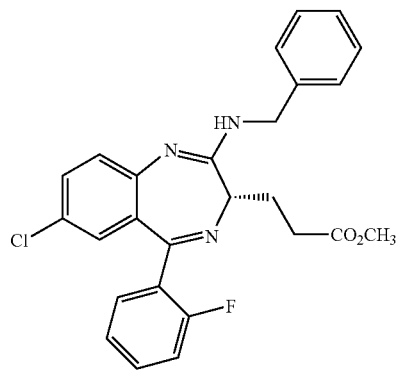

32%; $^1$H NMR (400 MHz, CDCl$_3$) δ 7.46-7.08 (m, 12H), 5.26 (bs, 1H), 4.68 (dd, 1H), 4.47 (dd, 1H), 3.67 (s, 3H), 3.29 (m, 1H), 2.80 (m, 1H), 2.52-2.31 (m, 3H). MS (ESI) m/z 464 (M+H)$^+$, base.

EXAMPLE Ib-5

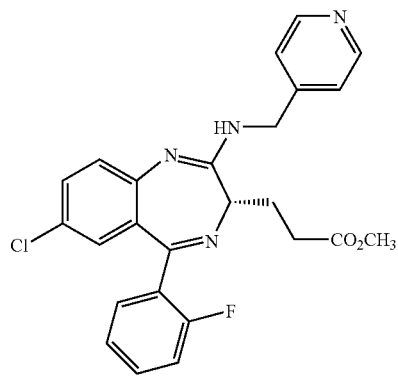

66%; $^1$H NMR (CDCl$_3$, 400 MHz) δ 8.50 (d, 2H, J=6.0 Hz), 7.42 (m, 2H), 7.34 (dd, 1H, J=8.7, 2.4 Hz), 7.25 (d, 1H, J=9.3 Hz), 7.14 (m, 2H), 7.11 (m, 3H), 5.60 (br s, 1H), 4.60 (d, 2H, J=4.8 Hz), 3.68 (s, 3H), 3.30 (dd, 1H, J=10.3, 3.1 Hz), 2,83 (m, 1H), 2.50 (m, 3H). MS (CI): 465 (M+H)$^+$.

EXAMPLE Ib-6

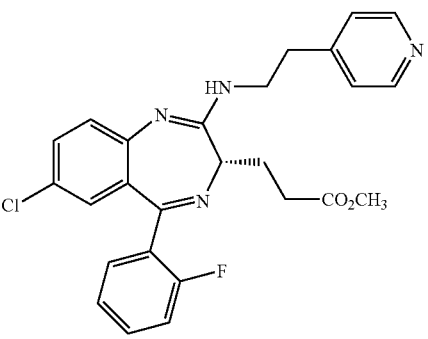

70%; $^1$H NMR (CDCl$_3$, 300 MHz) δ 8.52 (d, 2H, J=6.0 Hz), 7.46 (m, 3H), 7.27-7.10 (m, 6H), 5.28 (br s, 1H), 3.72 (br m, 5H), 3.28 (dd, 1H, J=9.9, 3.9 Hz), 2.98 (t, 2H, J=7.05 Hz), 2.70 (m, 1H), 2.48 (m, 2H), 2.32 (m, 1H). MS (CI): 479 (M+H)+.

EXAMPLE Ib-7

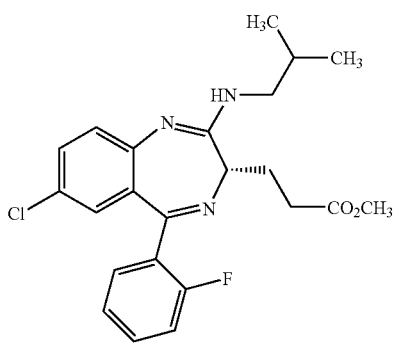

84%; ¹H NMR (CDCl₃, 300 MHz) δ 7.45 (t, 2H, J=6.9 Hz), 7.38 (dd, 1H, J=8.8, 2.2 Hz), 7.23 (m, 2H), 7.12 (m, 2H), 5.16 (br s, 1H), 3.74 (s, 3H), 3.30 (m, 3H), 2.85 (m, 1H), 2.50 (m, 3H), 1.92 (m, 1H), 0.98 (t, 6H, J=7.0 Hz). MS (ES): 429 (M+).

EXAMPLE Ib-8

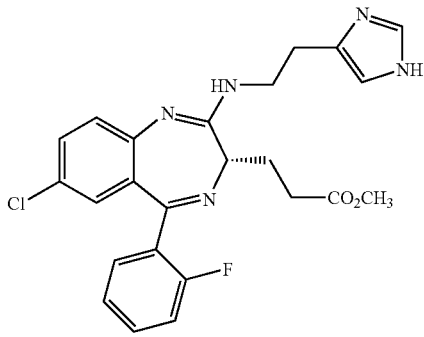

68%; ¹H NMR (CDCl₃, 300 MHz) δ 7.57 (s, 1H), 7.45 (m, 3H), 7.24 (m, 2H), 7.14 (m, 2H), 6.82

EXAMPLE Ib-9

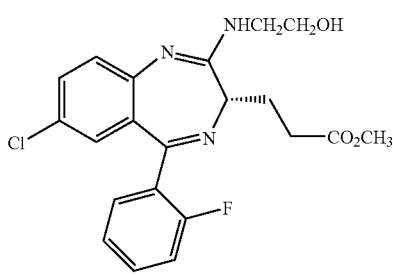

66%; ¹H NMR (CDCl₃, 400 MHz) δ 7.47 (m, 3H), 7.37 (m, 1H), 7.25 (t, 1H, J=7.2 Hz), 7.17 (m, 2H), 6.03 (br s, 1H), 3.85 (m, 3H), 3.74 (s, 3H), 3.51 (m, 1H), 3.39 (m, 1H), 2.83 (m, 1H), 2.48 (m, 3H). MS (CI): 418 (M+H)+.

EXAMPLE Ib-10

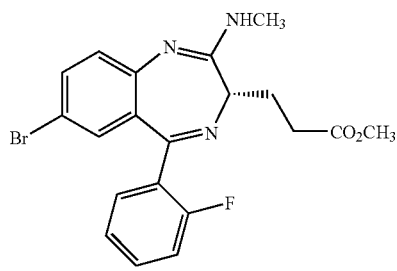

1.3 g of the iminophosphate Int-18 was dissolved in THF (10 mL) and treated with CH₃NH₂ (6 mL of a 2M THF solution, 12 mmol). After 3 hours the mixture was filtered and concentrated to an oil. Trituration with diisopropyl ether: hexanes provided Ib-10 as a white solid. ¹H NMR (400 MHz, CDCl₃) δ 7.50-7.06 (m, 7H), 5.15 (d, 1H), 3.70 (s, 3H), 2.95 (d, 3H), 2.79 (m, 1H), 2.53-2.31 (m, 3H).

Synthesis of Compounds of Formula Ic

General Procedure I: Swern Oxidation of Alcohols Using Oxalyl Chloride as Activating Agent.

A round-bottom flask was equipped with a stir bar and flushed with N₂. To the flask were added CH₂Cl₂ (5-15 mL/mmol of alcohol), dry dimethyl sulfoxide (DMSO, 3-4 mmol/mmol of alcohol) and the solution was cooled to −78° C. by means of a dry ice/acetone bath. Oxalyl chloride (2-3 mmol/mmol of alcohol) was added dropwise to the DMSO solution, taking care to maintain the reaction temperature below −50° C. When the addition was complete, the resulting solution was allowed to stir at −78° C. for 30 min. The Alcohol was dissolved in CH₂Cl₂ (2-3 mL/mmol of alcohol) and was carefully added to the DMSO solution at −78° C. The resulting mixture was allowed to stir at −78° C. for 2 h. Triethylamine (5-11 mmol/mmol of alcohol) was added and the mixture was allowed to warm to RT. When the reaction was judged to be complete, the mixture was poured into a separatory funnel containing water and CH₂Cl₂. The organic layer was collected and was washed with water, saturated aqueous brine, dried over Na₂SO₄, filtered and the solvents were removed under reduced pressure to provide the desired product which, in most cases, was used without further purification. If deemed necessary, the product was further purified by flash chromatography on silica gel.

General Procedure II: Swern Oxidation of Alcohols Using Trifluoroacetic Anhydride as Activating Agent.

Anhydrous DMSO (3-4 mmol/mmol of alcohol) was added to CH₂Cl₂ (5-15 mL/mmol of alcohol) and the solution was cooled to −78° C. Trifluoroacetic anhydride (2-3 mmol/mmol of alcohol) was added dropwise to the DMSO solution, taking care to maintain the reaction temperature below −50° C. When the addition was complete, the resulting solution was stirred at −78° C. for 30 min. A solution of the Alcohol in CH₂Cl₂ (2-3 mL/mmol of alcohol) was added carefully to the DMSO solution at −78° C. The reaction mixture was allowed to stir at −78° C. for 2 h, after which time it was allowed to warm to −35° C. for 5 min and was again cooled to −78° C. Et₃N (5-10 mmol/mmol of alcohol) was added and the stirring was continued at −78° C. for 30 min, after which time the reaction mixture was allowed to warm to RT. When the reaction was judged to be complete, the mixture was poured into a separatory funnel containing H₂O and CH₂Cl₂ and the layers were separated. The organic layer was washed with H₂O, brine, dried (MgSO₄), filtered and the solvents were removed under reduced pressure to provide the desired product which, in most cases, was used without further purification. If deemed necessary, the product was purified by flash chromatography on silica gel.

EXAMPLE Ic-1

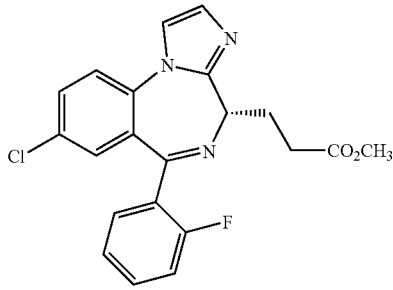

A mixture of alcohol (Example Ib-9, 200 mg, 0.48 mmol), DMSO (0.12 mL, 130 mg, 1.70 mmol), trifluoroacetic anhydride (0.12 mL, 180 mg, 0.84 mmol), CH₂Cl₂ (5 mL) and Et₃N (0.77 mL, 560 mg, 5.52 mmol) were used according to general procedure II. The product was purified by flash chromatography, elution with 1:1 hexane-EtOAc, to provide 70 mg (35%) of Ic-1 as a white solid: ¹H NMR (300 MHz, CDCl₃) δ 7.63 (m, 2H), 7.49 (m, 3H), 7.27 (m, 3H), 7.06 (t, 1H, J=9.3 Hz), 4.13 (m, 1H), 3.70 (s, 3H), 2.86 (m, 4H); MS (ES) m/z 398 (M+H)⁺.

EXAMPLE Ic-2

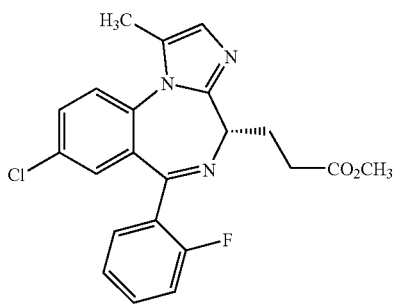

A mixture of alcohol (Int-5, 160 mg, 0.37 mmol), DMSO (90 μL, 0.10 g, 1.30 mmol), trifluoroacetic anhydride (90 μL, 0.14 g, 0.65 mmol), CH₂Cl₂ (5 mL) and Et₃N (0.60 mL, 0.43 g, 4.26 mmol) were used according to general procedure II. The resulting ketone closed to the imidazole during purification by flash chromatography, elution with 3:7 hexane-EtOAc, provide 50 mg (36%) of Ic-2 as a white solid: ¹H NMR (400 MHz, DMSO-d₆) δ 7.64 (t, 1H, J=7.4 Hz), 7.54 (dd, 1H, J=2.4, 8.8 Hz), 7.31 (m, 4H), 6.99 (t, 1H, J=9.3 Hz), 6.88 (s, 1H), 3.98 (m, 1H), 3.64 (s, 3H), 2.79 (m, 4H), 2.33 (s, 3H); MS (ESI) m/z 412 (M+H)⁺.

EXAMPLE Ic-3

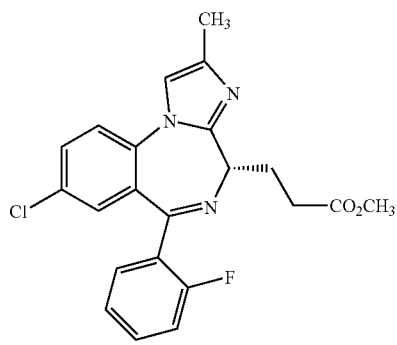

A mixture of alcohol (Int-6, 250 mg, 0.57 mmol), DMSO (0.14 mL, 160 mg, 2.00 mmol), trifluoroacetic anhydride (0.14 mL, 210 mg, 1.00 mmol), CH₂Cl₂ (5 mL) and Et₃N (0.92 mL, 670 mg, 6.60 mmol) were used according to general procedure II. The product was purified by flash chromatography, elution with 3:7 hexane-EtOAc, to provide 50 mg (22%) of Ic-3 as a pale yellow solid: ¹H NMR (400 MHz, CDCl₃) δ 7.59 (t, 1H, J=7.4 Hz), 7.52 (dd, 1H, J=2.2, 8.6 Hz), 7.41 (q, 2H, J=5.2, 13.6 Hz), 7.27 (d, 1H, J=2.0 Hz), 7.21 (m, 1H), 7.07 (s, 1H), 6.99 (m, 1H), 3.99 (m, 1H), 3.64 (s, 3H), 2.79 (m, 4H), 2.27 (s, 3H); MS (ESI) m/z 412 (M+H)⁺.

EXAMPLE Ic-4

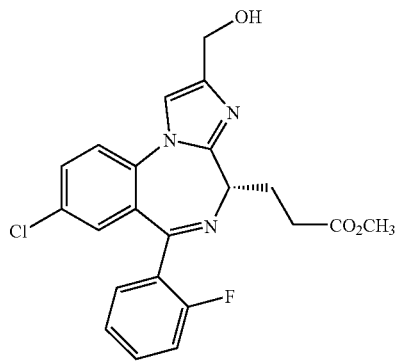

A mixture of diol (Int-7, 2.01 g, 4.49 mmol), TIPSCl (1.15 mL, 1.04 g, 5.39 mmol) Et₃N (0.69 mL, 500 mg, 4.94 mmol), and DMAP (60 mg, 0.45 mmol) in CH₂Cl₂ (20 mL) was stirred for 4-6 h. When the reaction was judged to be complete, the reaction mixture was poured into EtOAc, washed with H₂O (2×), brine, dried (Na₂SO₄), filtered and concentrated under reduced pressure. The product was isolated by flash chromatography, elution with CH₂Cl₂:MeOH (gradient 100:0-98:2), to provide 1.25 g (46%) of the silylether as an orange oil: ¹H NMR (400 MHz, CDCl₃) δ 7.42 (m, 2H), 7.34 (dd, 1H, J=2.4, 8.8 Hz), 7.13 (m, 4H), 6.03 (bs, 1H), 4.02 (m, 2H), 3.84 (s, 3H), 3.67 (s, 3H), 3.26 (m, 1H), 2.77 (m, 1H), 2.47 (m, 3H), 1.02 (m, 21H); MS (ESI) m/z 604 (M⁺).

A mixture of the silyl ether (1.25 g, 2.07 mmol), DMSO (0.59 mL, 650 mg, 8.28 mmol), (COCl)₂ (0.36 mL, 530 mg, 4.14 mmol), CH₂Cl₂ (15 mL) and Et₃N (3.20 mL, 2.30 g, 22.77 mmol) were used according to general procedure I. The product was purified by flash chromatography, elution with using CH₂Cl₂:MeOH (gradient, 100:0-95:5), to provide 1.05 g (87%) of the imidazole-silyl ether as an orange oil: MS (ESI) m/z 584 (M⁺). A mixture of this silyl ether (1.05 g, 1.79 mmol) and TBAF (2.05 mL of a 1.0 M solution in THF, 2.05 mmol) in THF (20 mL) was stirred for 1 h. When the reaction was judged to be complete, the mixture was poured into EtOAc, washed with H₂O, brine, dried (Na₂SO₄), filtered and concentrated under reduced pressure. The resulting yellow oil was treated with pentane to provide 500 mg (72%) of Ic-4 as a yellow solid: $^1$H NMR (400 MHz, DMSO-$d_6$) δ 7.76 (s, 2H), 7.66 (s, 1H), 7.54 (m, 2H), 7.29 (m, 2H), 7.17 (t, 1H, J=9.6 Hz), 5.02 (m, 1H), 4.36 (m, 2H), 4.03 (m, 1H), 3.56 (s, 3H), 2.61 (m, 4H); MS (ESI) m/z 427 (M⁺).

EXAMPLE Ic-5

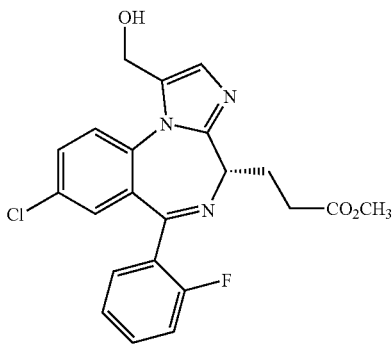

A mixture of diol (Int-8, 360 mg, 0.80 mmol), DMF (4 mL), CH₂Cl₂ (2 mL), Et₃N (0.2 mL, 150 mg, 1.43 mmol), and DMAP (10 mg, 0.12 mmol) was cooled to 0° C. and TBS-Cl chloride (190 mg, 1.27 mmol) was added as a solid in one portion. The reaction mixture was stirred at 0° C. for 2 h. The reaction mixture was poured into EtOAc, washed with H₂O, brine, dried (MgSO₄), filtered, and concentrated under reduced pressure to provide 340 mg (75%) of the monosilyl ether (primary hydroxyl) as a yellow foam: MS (CD m/z 562 (M+H)⁺. The silyl ether (340 mg, 0.60 mmol), DMSO (0.17 mL, 190 mg, 2.39 mmol), trifluoroacetic anhydride (0.17 mL, 250 mg, 1.20 mmol), CH₂Cl₂ (8 mL) and Et₃N (0.95 mL, 690 mg, 6.82 mmol) were used according to general procedure II. The product was purified by flash chromatography, elution with 1:1 hexane-EtOAc, to provide 140 mg (41%) of the ketone as a white solid: MS (CI) m/z 560 (M+H)⁺. A mixture of this ketone (130 mg, 0.232 mmol), DMF (4 mL) and p-toluenesulfonic acid monohydrate (30 mg, 0.14 mmol) was heated to 80° C. for 4 h, after which time the reaction was judged to be complete and was allowed to cool to RT. The mixture was poured into EtOAc, washed with H₂O, brine, dried (MgSO₄), filtered and concentrated under reduced pressure. The product was purified by flash chromatography, elution with 95:5 CH₂Cl₂:CH₃OH, to provide 70 mg (74%) of Ic-5 as a white solid: $^1$H NMR (300 MHz, CDCl₃) δ 8.10 (d, 1H, J=9.0 Hz), 7.65 (m, 2H), 7.46 (m, 1H), 7.34 (m, 2H), 7.20 (s, 1H), 7.04 (t, 1H, J=9.6 Hz), 4.90 (dd, 1H, J=13.5, 3.6 Hz), 4.49 (dd, 1H, J=13.3, 7.7 Hz), 4.10 (m, 1H), 3.70 (s, 3H), 2.83 (m, 4H), 1.81 (m, 1H). Anal. Calcd for C₂₂H₁₉ClFN₃O₃: C, 61.76; H, 4.48; N, 9.82. Found: C, 61.85; H, 4.56; N, 9.73.

EXAMPLE Ic-6

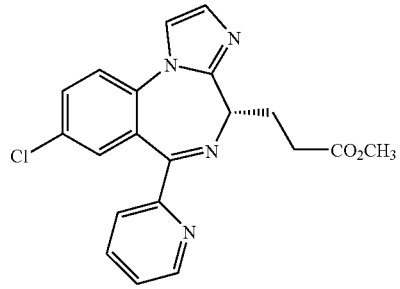

A mixture of alcohol (Int-14, 402 mg, 1.06 mmol), DMSO (0.30 mL, 330 mg, 4.24 mmol), (COCl)₂ (0.18 mL, 270 mg, 2.12 mmol), CH₂Cl₂ (7 mL) and Et₃N (1.60 mL, 1.20 g, 11.66 mmol) were used according to general procedure I. The product was isolated by flash chromatography, elution with using 2:1 hexane-acetone, to provide 140 mg (35%) of Ic-6 as a pale yellow solid: $^1$H NMR (300 MHz, DMSO-$d_6$) δ 8.52 (d, 1H, J=4.8 Hz), 8.10 (d, 1H, J=7.8 Hz), 7.97 (t, 1H, J=7.8 Hz), 7.82 (m, 3H), 7.52 (m, 2H), 7.11 (s, 1H), 4.18 (t, 1H, J=6.6 Hz), 3.64 (s, 3H), 2.71 (m, 4H).

The following examples were prepared according to General Procedure II set forth above in example Ic-6:

EXAMPLE Ic-7

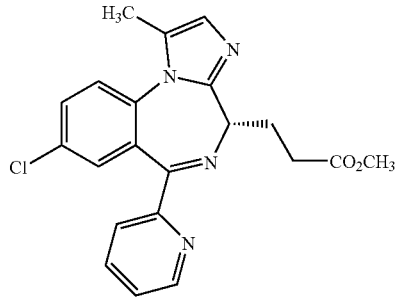

49%; $^1$H NMR (400 MHz, CDCl₃) δ 8.56 (d, J=4.6 Hz, 1H), 8.17 (d, J=7.7 Hz, 1H), 7.79 (dd, J=7.7, 1.6 Hz, 1H), 7.77 (d, J=1.6 Hz, 1H), 7.56 (dd, J=8.8, 2.4 Hz, 1H), 7.50 (d, J=2.4 Hz, 1H), 7.34 (comp, 2H), 6.86 9 s, 1H), 4.04 (m, 1H), 3.67 (s, 3H), 2.79 (m, 4H), 2.34 (s, 3H); ESIMS 395 (M+H, base); Anal. Cald. for C₂₁H₁₉ClN₄O₂. 0.5 MeOH: C, 62.85; H, 5.15; N, 13.64. Found: C, 62.99; H, 4.98; N, 13.54.

EXAMPLE Ic-8

Methyl 3-[(4S)-8-bromo-1-methyl-6-(2-pyridinyl)-4H-imidazo[1,2-a][1,4]benzodiazepin-4-yl]propanoate

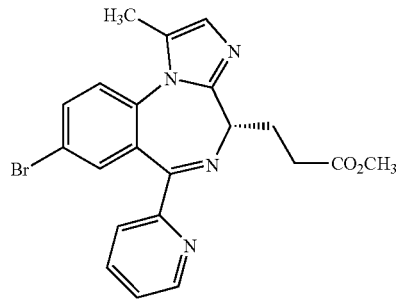

A solution of the C7-bromo-benzodiazepine Ex I-10 (7.31 g, 18.2 mmol) in THF (21 mL) was added to a suspension of NaH (870 mg of 60% oil dispersion, 21.8 mmol) in THF (70 mL) at 0° C. The reaction mixture was stirred at 0° C. for 30 min, warmed to room temperature and stirred for 30 min, then cooled to 0° C. Bis-morpholinophosphorochloridate (6.48 g, 25.5 mmol) was added, the mixture was allowed to warm to room temperature over 4.5 h, and the mixture was filtered with additional THF (ca. 10 mL). A mixture of the filtrate and DL-1-amino-2-propanol (2.80 mL, 36.4 mmol) was stirred at room temperature for 18 h and concentrated under reduced pressure. The residue was diluted with EtOAc (ca. 250 mL), washed with saturated aqueous NaHCO$_3$ (1×75 mL), H$_2$O (2×75 mL), saturated aqueous NaCl (1×75 mL), dried (Na$_2$SO$_4$), and concentrated under reduced pressure. Purification by flash chromatography, elution with 19:1 EtOAc-MeOH, gave 3.06 g (37%) of the adduct as a foam; ESIMS 459 (M+H, base).

A mixture of DMSO (1.88 mL, 26.6 mmol) and oxalyl chloride (1.16 mL, 13.3 mmol) in CH$_2$Cl$_2$ (40 mL) was stirred at −78° C. for 30 min. A solution of the alcohol prepared above (3.05 g, 6.64 mmol) in CH$_2$Cl$_2$ (26 mL) was added. The reaction mixture was warmed to −15° C. and stirred 1 h, cooled to −78° C., treated with Et$_3$N (5.55 mL, 39.9 mmol), and allowed to warm to room temperature over 3 h. The mixture was diluted with EtOAc (ca. 500 mL), washed with saturated aqueous NaHCO$_3$ (1×100 mL), H$_2$O (1×100 mL), saturated aqueous NaCl (1×100 mL), dried (Na$_2$SO$_4$), and concentrated under reduced pressure to give a foam. A mixture of this foam and a catalytic amount of p-toluenesulfonic acid was stirred at room temperature for 18 h, neutralized by the addition of saturated aqueous NaHCO$_3$ and diluted with EtOAc (ca. 500 mL). The layers were separated and the organic phase was washed with saturated aqueous NaHCO$_3$ (1×100 mL), H$_2$O (2×100 mL), saturated aqueous NaCl (1×100 mL), dried (Na$_2$SO$_4$), and concentrated under reduced pressure. Purification by flash chromatography, elution with 19:1 EtOAc-MeOH, gave 2.56 g (88%) of Ic-8 as a foam; $^1$H NMR (400 MHz, CDCl$_3$) δ 8.57 (d, J=4.6 Hz, 1H), 8.17 (d J=7.8 Hz, 1H), 7.79 (dd, J=7.7, 6.2 Hz, 1H), 7.71 (dd, J=8.6, 2.2 Hz, 1H), 7.64 (d, J=2.2 Hz, 1H), 7.34 (dd, J=7.5, 5.0 Hz, 1H), 7.30 (d, J=8.6 Hz, 1H), 6.86 (s, 1H), 4.05 (m, 1H), 3.67 (s, 3H), 2.80 (comp, 4H), 2.34 (s, 3H); ESIMS 461 (M+Na, base), 439 (M+H); Anal. calcd. for C$_{21}$H$_{19}$BrN$_4$O$_2$.0.25H$_2$O: C, 58.63; H, 4.43; N, 12.62. Found: C, 56.88; H, 4.43; N, 12.23.

Example Ic-8 was formulated in an aqueous vehicle at a concentration of 10 mg/ml. Accordingly, 10 mg of compound (and 9 mg NaCl) was dissolved in 0.63 ml of 0.1 N HCl. Slowly and while stirring, 0.37 ml of 0.1 N NaOH was added. Adjustments are made to the dose volume depending on the dose being administered.

The following example was prepared according to General Procedure I set forth above in example Ic-8:

EXAMPLE Ic-9

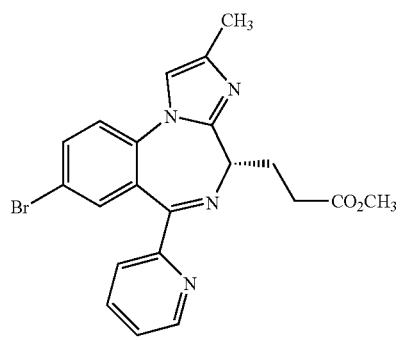

EXAMPLE Ic-10

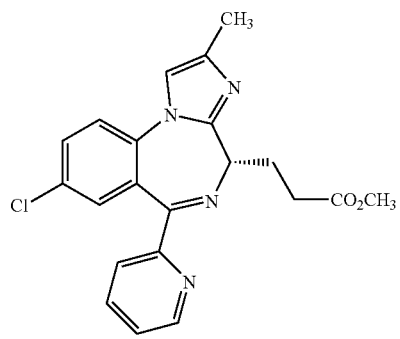

49%; $^1$H NMR (400 MHz, CDCl$_3$) δ 8.54 (d, J=4.8 Hz, 1H), 8.13 (d, J=7.8 Hz, 1H), 7.79 (dd, J=7.8, 1.7 Hz, 1H), 7.55 (dd, J=8.6, 2.4 Hz, 1H), 7.43 (comp, 2H), 7.33 (dd, J=6.8, 4.8 Hz, 1H), 7.03 (s, 1H), 4.08 (m, 1H), 3.67 (s, 3H), 2.80 (m, 4H), 2.26 (s, 3H); ESIMS 395 (M+H, base); Anal. Cald. for C$_{21}$H$_{19}$ClN$_4$O$_2$.0.5 MeOH: C, 62.85; H, 5.15; N, 13.64. Found: C, 62.96; H, 5.13; N, 13.33.

The following example was prepared according to the procedure set forth in example Ic-4:

EXAMPLE Ic-11

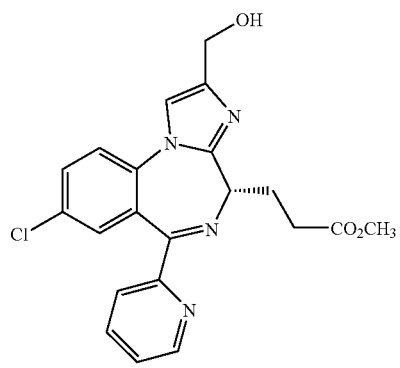

51%; $^1$H NMR (300 MHz, DMSO-d$_6$) δ 8.52 (d, 1H, J=4.8 Hz), 8.09 (d, 1H, J=7.8 Hz), 7.97 (t, 1H, J=7.6 Hz), 7.78 (m,

2H), 7.67 (s, 1H), 7.50 (m, 2H), 5.05 (bs, 1H), 4.40 (s, 2H), 4.16 (m, 1H), 3.64 (s, 3H), 2.70 (m, 4H); MS (ESI) m/z 410 (M+).

The following example was prepared according to the procedure set forth in Example Ic-5:

EXAMPLE Ic-12

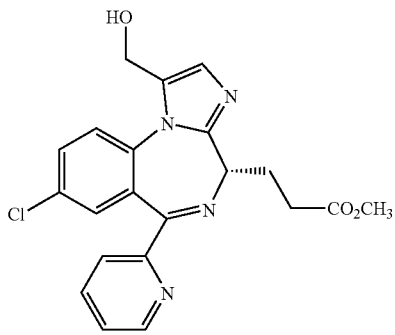

45%; ¹H NMR (300 MHz, CDCl₃) δ 8.54 (d, 1H, J=4.5 Hz), 8.14 (d, 1H, J=7.8 Hz), 8.05 (d, 1H, J=8.7 Hz), 7.80 (t, 1H, J=7.8 Hz), 7.60 (dd, 1H, J=9, 2.4 Hz), 7.45 (d, 1H, J=2.4 Hz), 7.34 (m, 1H), 7.12 (s, 1H), 4.79 (d, 1H, J=12.9 Hz), 4.45 (d, 1H, J=12.9 Hz), 4.10 (m, 1H), 3.67 (s, 3H), 2.80 (m, 4H). MS (ES) m/z 410 (M+).

EXAMPLE Ic-13

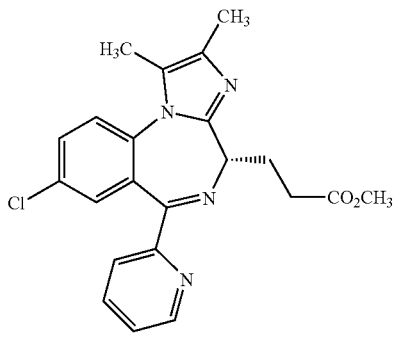

A mixture of alcohol (Int-13, 620 mg, 1.43 mmol), DMSO (0.40 mL, 5.64 mmol), trifluoroacetic anhydride (0.40 mL, 2.83 mmol), Et₃N (2.00 mL, 14.4 mmol) and CH₂Cl₂ were used according to general procedure II. The intermediate ketone was used without purification. A mixture of the ketone and p-toluenesulfonic acid (80 mg, 0.42 mmol) in DMF (5 mL) was heated at 80° C. for 30 min. After the reaction was judged to be complete, it was allowed to cool to RT and was poured into EtOAc, washed with H₂O, brine, dried (MgSO₄), filtered and concentrated under reduced pressure. The product was purified by flash chromatography, elution with 2:1 hexane-acetone, to provide 210 mg (41%) of Ic-13 as a tan solid: ¹H NMR (300 MHz, CDCl₃) δ 8.56 (d, 1H, J=4.8 Hz), 8.17 (d, 1H, J=8.1 Hz), 7.78 (m, 1H), 7.55 (dd, 1H, J=8.7, 2.4 Hz), 7.49 (m, 1H), 7.31 (m, 2H), 4.0 (m, 1H), 3.66 (s, 3H), 2.80 (m, 4H), 2.25 (s, 3H), 2.19 (s, 3H); MS (ESI): m/z 408 (M+).

EXAMPLE Ic-14

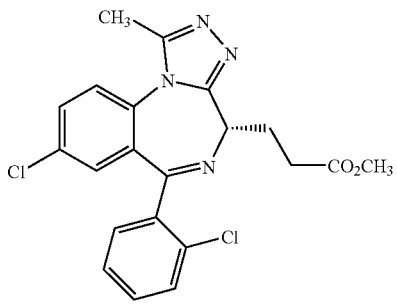

To a solution of thiolactam Ex I-29 (203 mg, 0.5 mmol) in CH₂Cl₂ (1 mL) was added trimethyloxonium tetrafluoroborate (74 mg, 0.8 mmol). The solution was stirred for 1 hr and diluted with CH₂Cl₂ (50 mL). The solution was washed with sat NaHCO₃ and brine, dried over MgSO₄, filtered, and concentrated. Flash chromatography (4:1 hexanes:ethyl acetate) provided 112 mg of the methylthioimidate as a white foam. ¹H NMR (400 MHz, CDCl₃) δ 2.46 (s, 3H). MS (ESI): m/z 421 (M+H⁺, base).

A solution of the methylthioimidate (174 mg, 0.4 mmol) and acetic hydrazide (31 mg, 0.4 mmol) in DCE (1 mL) was heated at 100 C for 16 hr. The dark brown mixture was evaporated and the residue was chromatographed (graded elution with 3:2 CH₂Cl₂:ether to 3:2 CH₂Cl₂:ether with 2% methanol) to yield, upon trituration with diisopropyl ether, 49 mg of Ic-14 as a tan powder. ¹H NMR (400 MHz, CDCl₃) δ 4.25 (m, 1H), 3.65 (s, 3H), 2.61 (s, 3H). MS (ESI): m/z 429 (M+H⁺, base).

The following example was prepared according to the procedure set forth above in Example Ic-14:

EXAMPLE Ic-15

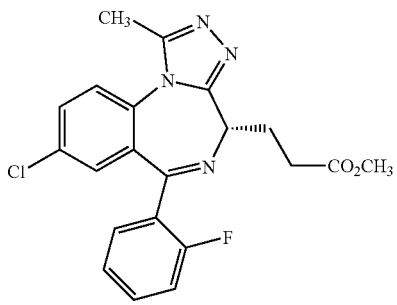

¹H NMR (400 MHz, CDCl₃) δ 4.21 (m, 1H), 3.66 (s, 3H), 2.66 (s, 3H). MS (AP+): m/z 429 (M+Na⁺, base).

EXAMPLE Ic-16

Example Ic-16 was prepared using Otera's catalyst, sec-butyl alcohol, and methyl ester Ic-15 according to the procedure set forth in Example I-14.

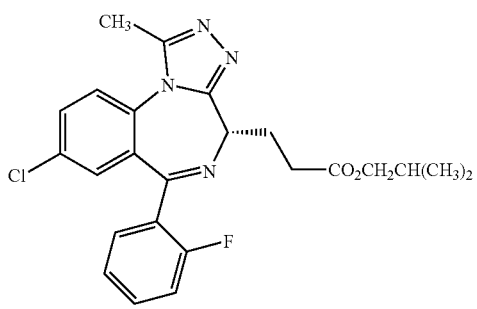

96%; $^1$H NMR (400 MHz, CDCl$_3$) δ4.22 (m, 1H), 3.83 (d, 2H), 2.66 (s, 3H), 1.88 (m, 1H), 0.88 (d, 6H).

EXAMPLE Ic-17

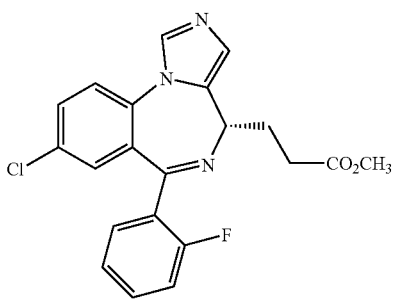

In a round-bottomed flask was dissolved Int-17 (0.84 g, 1.69 mmol) in methylene chloride (10 mL). To this was added trifluoroacetic acid (8.00 mL) and the resulting solution was stirred overnight at room temperature. The reaction was concentrated to dryness and the residue was taken up in a 0.5 M sodium carbonate solution. The aqueous layer was washed twice with chloroform and once with diethyl ether (filtration through Celite was used to break up any emulsions). The aqueous layer was then adjusted to a pH of 4.5 using 1M phosphoric acid. The water layer was then extracted with ethyl acetate and chloroform. The combined organic extracts were dried over magnesium sulfate, filtered and concentrated to give the carboxylic acid (0.47 g, 1.06 mmol) which was dissolved in 1,2,4-trichlorobenzene and heated to reflux (214° C.) for 30 min. The reaction was cooled to room temperature and loaded onto a silica gel pad. The pad was eluted with chloroform then the product was eluted with 3% methanol in chloroform to provide Ic-17 (0.35 g, 0.88 mmol). $^1$H NMR (CDCl$_3$): 8.05 (br s, 1H), 7.52-7.6 (m, 3H), 7.4-7.46 (m, 1H), 7.27 (d, 1H, J=1.6 Hz), 7.22 (t, 1H, J=7.8 Hz), 7.0-7.19 (m, 2H), 4.15 (dd, 1H, J=3.6, 5.2 Hz), 3.69 (s, 3H), 2.74-2.84 (m, 1H), 2.62-2.73 (m, 2H), 2.50-2.60 (m, 1H). MS (ES+)=398(100%, M+).

EXAMPLE Ic-18

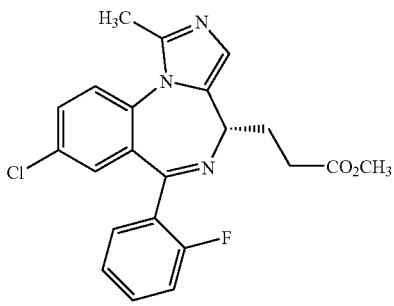

t-Butyl acrylate (45 mL) was added to a stirred solution of 3.25 g (10 mmol) midazolam in 20 ml THF. The solution was cooled to −15° C., and 20 ml 1.0M solution of potassium t-butoxyde in t-butanol was added over 10 min. The mixture was stirred for 1 h at −10° C., then diluted with 500 ml ether. The solution was washed with brine 3 times, dried with anhydrous magnesium sulfate and concentrated under reduced pressure. The residue was purified using silica gel chromatography (hexane-ethyl acetate (1:1)), providing 2.55 g of the ester. (56%) $^1$H-NMR (CDCl$_3$) δ 7.7-6.9 m (8H), 3.95 dd (J=4.7, 9.0, 1H), 2.7-2.4 m (4H), 2.51 s (3H), 1.39 s (9H). MS: 454 (M+1, ES+).

TFA (100 mL) was added to a stirred solution of 2.42 g (5.3 mmol) tBu ester in methylene chloride (100 mL). The mixture was stirred at 20° C. for 2 h, then concentrated under reduced pressure. The residue was dissolved in chloroform (300 ml) then the solvent was evaporated. 50 ml DMF, 10 g potassium carbonate and 1.5 g methyl iodide was added to the residue, then the reaction was stirred at 20° C. for 90 min. The mixture was diluted with 300 ml ether, extracted with 200 ml water five times, and the organic phase was dried with anhydrous magnesium sulfate and concentrated under reduced pressure. 10 ml ether was added to the residue, and the solution was stirred at 0° C. for 30 min. The white powder was filtered and dried under vacuum to obtain 1.07 g of rac-Ic-18. (49%) $^1$H-NMR (CDCl$_3$): δ 7.60 m (2H), 7.40 m (2H), 7.22 m (2H), 7.00 t (J=10, 1H), 6.90 s (1H), 4.03 dd (J=4.8, 9.0, 1H), 3.68 s (3H), 2.8-2.4 m (4H), 2.54 s (3H). MS: 412 (M+1, ES+).

Separation of the enantiomers of rac-Ic-18 can be performed by preparative chiral chromatography (Daicel AD column 5×50 cm, 20 micron; 20% IPA/Hexane, 50-80 ml/min, UV 270 nM). The two enantiomers have the following optical properties: (+)-Ic-18 t$_{ret}$: 13.5 min., [α]$_D$=+13.3 (THF, c=25 mg/ml); (−)-Ic-18: t$_{ret}$: 21.8 min, [α]$_D$=−13.2 (THF, c=29 mg/ml).

EXAMPLE Ic-19

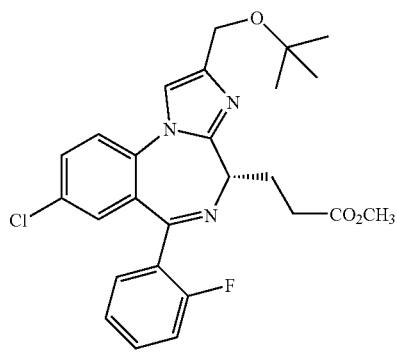

To the iminophosphate Int-19 (15 g) was added a 50 mL of 1M THF solution of DL-serinol, t-butyl ether (prepared according to Meyers et al. *J. Org. Chem.* 1993, 58, 3568). Stirred at rt for 16 h, added an additional 2 equiv. of amino alcohol. Heated to reflux for 1.5 h then standard aqueous extractive workup (DCM). Flash chromatography (3:1, hexanes:acetone) provided 7.7 g (62%) of the intermediate amidine. The amidine was converted to example Ic-19 using general procedure I, followed by a TsOH/DMF cyclodehydration step as described in example Ic-5. $^1$H NMR (400 MHz, CDCl$_3$) δ 4.50 (dd, 2H), 4.03 (m, 1H), 3.66 (s, 3H), 1.29 (s, 9H). MS (ES): 484 (M+1$^+$).

When used in medicine, the salts of a compound of the invention should be pharmaceutically acceptable, but pharmaceutically unacceptable salts may conveniently be used to prepare the corresponding free base or pharmaceutically acceptable salts thereof. Such pharmaceutically acceptable salts include, but are not limited to, those prepared from the following acids: hydrochloric, hydrobromic, sulfuric, nitric, phosphoric, salicylic, p-toluenesulfonic, tartaric, citric, methanesulfonic, maleic, formic, malonic, succinic, isethionic, lactobionic, naphtalene-2-sulfonic, sulfamic, ethanesulfonic and benzenesulfonic.

Moreover, while it is possible for the compounds of the invention to be administered as the bulk active chemicals, it is preferably presented with an acceptable carrier in the form a pharmaceutical formulation. The carrier must, of course, be acceptable in the sense of being compatible with the other ingredients of the formulation and must not be deleterious to the recipient. Accordingly, the present invention provides a pharmaceutical formulation which comprises a compound of Formula (I) as hereinbefore defined and a pharmaceutically acceptable carrier in the form a pharmaceutical formulation. The formulations include those suitable for oral, rectal, topical, buccal (e.g. sub-lingual) and parenteral (e.g., subcutaneous, intramuscular, intradermal or intravenous) administration. It is preferred to present compounds of the present invention in the form of a pharmaceutical formulation for parenteral administration, e.g., by intravenous or intramuscular injection of a solution. Where the pharmaceutical formulation is for parenteral administration, the formulation may be an aqueous or non-aqueous solution or mixture of liquids, which may contain bacteriostatic agents, antioxidants, buffers or other pharmaceutically acceptable additives. The preferred formulations of compounds of Formula (I) of the present invention is by either an aqueous acidic medium of pH 2-4 or by use of an aqueous solution of a cyclodextrin. Cyclodextrins that can be used for these formulations are either the anionically charged sulfobutylether (SBE) derivatives of β-CD, specifically SBE7-β-CD, marketed under the tradename Captisol by CyDex, Inc. (*Critical Reviews in Therapeutic Drug Carrier Systems*, 14 (1), 1-104 (1997)), or the hydroxypropyl CD's. The preferred method of formulation (i.e., acid buffer or CD-based) may depend on the physicochemical properties (e.g., aqueous solubility, pKa, etc.) of a particular compound. Alternatively the compounds may be presented as lyophilized solids for reconstitution with water (for injection) or dextrose or saline solutions. Such formulations are normally presented in unit dosage forms such as ampoules or disposable injection devices. They may also be presented in multi-dose forms such as a bottle from which the appropriate dose may be withdrawn. All such formulations should be sterile.

Accordingly, the present invention also provides a method for producing sedation or hypnosis in a mammal, which comprises administering to the mammal an effective sedative or hypnotic amount of a compound of the present invention as hereinbefore defined. The present invention also provides a method for inducing anxiolysis in a mammal, which comprises administering to the mammal an effective anxiolytic amount of a compound of the present invention as hereinbefore defined. The present invention also provides a method for inducing muscle relaxation in a mammal, which comprises administering to the mammal an effective muscle relaxant amount of a compound of the present invention as hereinbefore defined. The present invention also provides a method for treating convulsions in a mammal, which comprises administering to the mammal an effective anticonvulsant amount of a compound of the present invention as hereinbefore defined.

The present invention also provides the use of a sedative or hypnotic amount of a compound of the present invention as hereinbefore defined in the manufacture of a medicament for producing sedation or hypnosis in a mammal, including in a human. The present invention also provides the use of a anxiolytic amount of a compound of the present invention as hereinbefore defined in the manufacture of a medicament for producing anxiolysis in a mammal, including in a human. The present invention also provides the use of a muscle relaxant amount of a compound of the present invention as hereinbefore defined in the manufacture of a medicament for producing muscle relaxation in a mammal, including in a human. The present invention also provides the use of an anticonvulsant amount of a compound of the present invention as hereinbefore defined in the manufacture of a medicament for treating convulsions in a mammal, including in a human.

Intravenous administration can take the form of bolus injection or, more appropriately, continuous infusion. The dosage for each subject may vary, however, a suitable intravenous amount or dosage of the compounds of the present invention to obtain sedation or hypnosis in mammals would be 0.01 to 5.0 mg/kg of body weight, and more particularly, 0.02 to 0.5 mg/kg of body weight, the above being based on the weight of the compound which is the active ingredient. A suitable intravenous amount or dosage of the compounds of the present invention to obtain anxiolysis in mammals would be 0.01 to 5.0 mg/kg of body weight, and more particularly, 0.02 to 0.5 mg/kg of body weight, the above being based on the weight of the compound which is the active ingredient. A suitable intravenous amount or dosage of the compounds of the present invention to obtain muscle relaxation in mammals would be 0.01 to 5.0 mg/kg of body weight, and more particularly, 0.02 to 0.5 mg/kg of body weight, the above being based on the weight of the compound which is the active ingredient. A suitable intravenous amount or dosage of the compounds of the present invention to treat convulsions in mammals would be 0.01 to 5.0 mg/kg of body weight, and more particularly, 0.02 to 0.5 mg/kg of body weight, the above being based on the weight of the compound which is the active ingredient.

Thus a suitable pharmaceutical parenteral preparation for administration to humans will preferably contain 0.1 to 20 mg/ml of a compound of the present invention in solution or multiples thereof for multi-dose vials.

The compounds of the present invention elicit important and measurable pharmacological responses. The compounds described by this invention bind with high affinity to the benzodiazepine site on the GABA$_A$ receptor complex ("benzodiazepine receptor"). The binding affinity was measured by use of the following benzodiazepine radioligand binding assay.

Tissues: Membrane homogenates were prepared from male Sprague Dawley rat brain (whole brain less cerebellum), female Yucatan micropig brain cortex and female human brain cortex according to the methods described by Marangos & Martinos (Molecular Pharmacology 20:16-21, 1981). The human donor was a 72 year old female Caucasian who died of an acute cardiopulmonary aneurysm. All tissues were obtained from, and membrane homogenates were prepared by Analytical Biological Services (ABI, Wilmington, Del.). Homogenates were frozen, stored at minus 80° C. and thawed immediately before use in radioligand binding assays.

Materials: $^3$H-flunitrazepam (NET-567) was obtained from New England Nuclear, Boston, Mass. 2'-chlorodiazepam was prepared at Glaxo Wellcome, RTP, USA. Tris HCl was obtained from GibcoBRL and sodium chloride was obtained from J. T. Baker. Microscint-20 liquid scintillant and Unifilter 96 well plates were purchased from Packard Instruments. Midazolam and chlordiazepoxide were purchased from Sigma Chemicals. Flumazenil was a gift from Hoffman LaRoche.

Assay conditions: Test compounds were prepared in 100% DMSO at a concentration of 25-50 mM. Compounds were diluted in assay buffer such that the first well contained 100 μM (final concentration). Eleven 3-fold serial dilutions were prepared in buffer to complete a 12-point concentration-response curve for each test compound. Each concentration was tested in triplicate and compounds of interest were tested on at least 3 separate occasions. The final concentration of DMSO in each well did not exceed 0.4%. Nonspecific binding was defined in the presence of 10 μM 2'-chlorodiazepam (Ki=0.5 nM). The final concentrations of $^3$H-flunitrazepam were 2 nM, 2 nM and 2.5 nM for rat, micropig and human assays, respectively. The concentrations differed slightly among the tissues so that the signal-to-noise ratio was optimized and the lowest possible concentration was used. Concentration-response curves for midazolam, chlordiazepoxide or flumazenil were conducted as controls with each assay run. Radioligand, compounds and membrane homogenates were incubated for 90 minutes at 4° C. in buffer consisting of 50 mM Tris HCl, pH 7.4, containing 150 mM NaCl. All assays were conducted in 96 well plates in a total assay volume of 200 mL. Protein concentrations were 12, 9 and 15 micrograms/well for rat, pig and human preparations, respectively. The reaction was terminated by rapid filtration (Packard Filtermate-196) through 96-well GF/B filter plates (Packard # 6005177). The filters were washed 8 times with 200 μL/well with ice-cold Tris 50 mM, pH7.4 (~1.6 ml total). After drying, 20 μL of Microscint was added to each well and the plates were sealed. Plates were counted using a Packard TopCount microtiter plate scintillation counter.

Data analysis: Data were analyzed, fitted to a single site equation, and $IC_{50}$ values were calculated using the Excel Addin Robosage (Glaxo Wellcome Research Information Resources). Ki values were calculated using the equation of Cheng and Prusoff (Biochem. Pharmacol. 22:3099-3108, 1973). Kd values of $^3$H-flunitrazepam used in Ki calculations were determined for each tissue in saturation binding experiments.

TABLE 1

Benzodiazepine receptor binding (Ki measured in nM; 1-50 nM = ++++; 51-100 nM = +++; 101-1000 nM = ++; >1,000 = +)

| Example No. | Ki (nM) |
|---|---|
| 1-1 | ++++ |
| 1-2 | +++ |
| 1-3 | ++++ |
| 1-4 | ++ |
| 1-5 | ++++ |
| 1-6 | ++ |
| 1-7 | ++++ |
| 1-8 | ++++ |
| 1-9 | ++ |
| 1-10 | +++ |
| 1-11 | ++ |

TABLE 1-continued

Benzodiazepine receptor binding (Ki measured in nM; 1-50 nM = ++++; 51-100 nM = +++; 101-1000 nM = ++; >1,000 = +)

| Example No. | Ki (nM) |
|---|---|
| 1-12 | ++ |
| 1-13 | ++++ |
| 1-14 | ++ |
| 1-15 | ++ |
| 1-16 | ++++ |
| 1-17 | ++ |
| 1-18 | ++ |
| 1-19 | ++ |
| 1-20 | ++++ |
| 1-21 | ++++ |
| 1-22 | ++ |
| 1-23 | ++++ |
| 1-24 | +++ |
| 1-25 | +++ |
| 1-26 | +++ |
| 1-27 | ++++ |
| 1-31 | +++ |
| 1b-1 | +++ |
| 1b-2 | + |
| 1b-3 | ++ |
| 1b-4 | ++ |
| 1b-5 | + |
| 1b-6 | ++ |
| 1b-7 | + |
| 1b-8 | ++ |
| 1b-9 | ++ |
| 1b-10 | ++++ |
| 1c-1 | ++++ |
| 1c-2 | ++++ |
| 1c-3 | ++++ |
| 1c-4 | ++++ |
| 1c-5 | ++++ |
| 1c-6 | +++ |
| 1c-7 | +++ |
| 1c-8 | ++++ |
| 1c-9 | ++++ |
| 1c-10 | +++ |
| 1c-11 | ++ |
| 1c-12 | ++ |
| 1c-13 | ++ |
| 1c-14 | ++++ |
| 1c-15 | ++++ |
| 1c-16 | ++++ |
| 1c-17 | ++ |
| 1c-18 | ++++ |
| 1c-19 | ++++ |

High affinity binding of a ligand to the benzodiazepine receptor does not characterize the intrinsic efficacy (full agonist, inverse agonist, antagonist) of a benzodiazepine receptor ligand. The intrinsic efficacy of a compound was assessed by its ability to cause loss of the righting reflex (LRR) in rats, an effect associated with benzodiazepine full agonism.

Method: Subjects for these studies were male Wistar rats, weighing approximately 250-350 grams. To assess loss of righting reflex (LRR), animals were placed in plastic restrainers and test compounds were administered i.v. via the tail vein. Subjects were immediately removed from the restrainer and the time to onset of loss of righting reflex was recorded. LRR was defined as the loss of an animal's ability to right itself when placed in a supine position. A compound was identified as inactive in this model if LRR was not observed within 5 minutes following injection. Compounds producing LRR were evaluated by three measures: 1) Time to onset of LRR (as described above) 2) Time to recover from LRR. An animal met this criteria when able to right itself three consecutive times after losing its righting reflex 3) Total recovery time. Total recovery was measured by the animal's ability to walk without ataxia as well as its ability to pull itself up three consecutive times when suspended from a horizontal wire. Compounds producing loss-of-righting at a dose in the range of 10-100 mg/kg include the following: examples 1, 3, 4, 5, 6, 7, 9, 11, 17, 23 of compounds of Formula Ia, examples 1 and 10 of compounds of Formula Ib and examples 1, 2, 3, 6, 7, 8, 10, 14, 15, 17, 18 of compounds of Formula Ic. In the rat loss-of-righting model at a dose range of 10-100 mg/kg, the compounds of this invention displayed overt pharmacological responses similar to those of therapeutically useful benzodiazepines described in the prior art. The therapeutically useful dosage range for administration to mammals is 0.01 to 5.0 mg/kg of body weight.

What is claimed is:

1. A compound of formula (I):

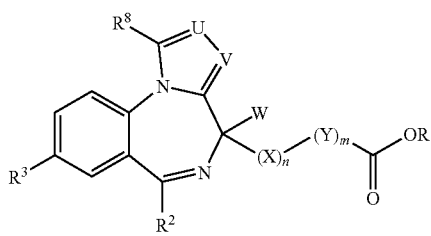

Formula (I)

wherein

W is H, a $C_1$-$C_4$ branched alkyl, or straight chained alkyl;
X is $CH_2$, NH or $NCH_3$; n is 1 or 2;
Y is O or $CH_2$; m is 0 or 1, provided that if X is $CH_2$, n is 1 and m is 0, then $R^1$ is not $CH_2CH_3$;
$R^1$ is H, a $C_1$-$C_7$ straight chain alkyl, a $C_3$-$C_7$ branched chain alkyl, a $C_{1-4}$haloalkyl, a $C_3$-$C_7$ cycloalkyl, an aryl, a heteroaryl, an aralkyl, or a heteroaralkyl;
$R^2$ is phenyl, 2-halophenyl or 2-pyridyl,
$R^3$ is H, Cl, Br, F, I, $CF_3$ or $NO_2$;
$R^8$ is hydrogen, $C_{1-4}$alkyl or $C_{1-3}$hydroxyalkyl;
U is $CR^9$ where $R^9$ is H, $C_{1-3}$hydroxyalkyl, $C_{1-4}$alkoxy, or $C_{1-4}$alkyl;
and V is CH;
or a pharmaceutically acceptable salt or solvate thereof.

2. A compound of claim 1 wherein
W is H;
X is $CH_2$, n is 1;
Y is $CH_2$, m is 1;
$R^1$ is $CH_3$ or $CH_2CH(CH_3)_2$;
$R^2$ is 2-fluorophenyl, 2-chlorophenyl or 2-pyridyl;
$R^3$ is Cl or Br; and
$R^8$ is H, $CH_3$ or $CH_2OH$.

3. A pharmaceutical composition comprising a pharmaceutically acceptable carrier and an effective amount of a compound of claim 1.

4. A pharmaceutical formulation composition comprising a pharmaceutically acceptable carrier and an effective amount of a compound of claim 2.

5. A method of producing sedation or hypnosis, inducing anxiolysis, inducing muscle relaxation in a mammal, or treating convulsions in a mammal, comprising:
administering to the mammal an effective amount of a compound of claim 1.

6. The method of claim 5 wherein the mammal is in need of sedation.

7. The method of claim 5 wherein the mammal is in need of hypnosis.

8. The method of claim 5 wherein the mammal is in need of muscle relaxation.

9. The method of claim 5 wherein the mammal suffers from convulsions.

10. A method of providing sedation or hypnosis, inducing anxiolysis, inducing muscle relaxation in a mammal, or treating convulsions in a mammal, comprising:
administering to the mammal an effective amount of a compound of claim 2.

* * * * *